(12) United States Patent
Pollard et al.

(10) Patent No.: US 6,794,147 B1
(45) Date of Patent: Sep. 21, 2004

(54) METHODS FOR IDENTIFYING CONTRACEPTIVE COMPOUNDS

(75) Inventors: Jeffrey W. Pollard, New York, NY (US); Winfried Edelmann, Bronx, NY (US); Paula E. Cohen, Bronx, NY (US); Burkhard Kneitz, Wurzburg (DE); Panos Stevis, Glenmoore, PA (US); Raju S. Kucherlapati, Boston, MA (US)

(73) Assignees: Wyeth, Madison, NJ (US); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/991,099

(22) Filed: Nov. 21, 2001

Related U.S. Application Data

(60) Provisional application No. 60/252,661, filed on Nov. 22, 2000.

(51) Int. Cl.⁷ .............................................. G01N 33/53
(52) U.S. Cl. .................................. 435/7.1; 435/4; 435/6
(58) Field of Search .................................. 435/4, 6, 7.1

(56) References Cited

FOREIGN PATENT DOCUMENTS

| WO | WO 99/01550 A1 | 1/1999 |
| WO | WO 99/10369 A1 | 3/1999 |

OTHER PUBLICATIONS

Pochart et al. Journal of Biological Chemistry 272: 30345–30349, 1997.*
van Nocker et al. Molecular and Cellular Biology 16:6020–6028, 1996.*
Fu et al. Journal of Biological Chemistry 273: 1970–1981, 1998.*
Bocker T et al. hMSH5: a human MutS homologue that forms a novel heterodimer with hMSH4 and is expressed during spermatogenesis. Cancer Res. Feb. 15, 1999; 59(4):816–22.
Cohen PE et al. Regulation of meiotic recombination and prophase I progression in mammals. Bioessays. Nov. 2001; 23(11):996–1009.
Khazanehdari KA Borts RH.EXO1 and MSH4 differentially affect crossing–over and segregation. Chromosoma. 2000; 109(1–2):94–102.
Kneitz B et al. MutS homolog 4 localization to meiotic chromosomes is required for chromosome pairing during meiosis in male and female mice. Genes Dev. May 1, 2000; 14(9):1085–97.
Paquis–Flucklinger V et al. Cloning and expression analysis of a meiosis–specific MutS homolog: the human MSH4 gene. Genomics. Sep. 1, 1997; 44(2):188–94.
Winand NJ et al. Cloning and characterization of the human and Caenorhabditis elegans homologs of the Saccharomyces cerevisiae MSH5 gene. Genomics. Oct. 1, 1998; 53(1):69–80.
Zalevsky J et al. Crossing over during Caenorhabditis elegans meiosis requires a conserved MutS–based pathway that is partially dispensable in budding yeast. Genetics. Nov. 1999 ; 153(3):1271–83.
Gen Bank Accession AF104243, Homo sapiens meiosis–specific MutS homolog (MSH4) mRNA, complete cds. (Mar. 4, 1999).
Hollingsworth NM et al. MSH5, a novel MutS homolog, facilitates meiotic reciprocal recombination between homologs in Saccharomyces cerevisiae but not mismatch repair. Genes Dev. Jul. 15, 1995 ; 9(14):1728–39.

* cited by examiner

*Primary Examiner*—James Ketter
*Assistant Examiner*—David A. Lambertson
(74) *Attorney, Agent, or Firm*—Lahive & Cockfield LLP; Amy E. Mandragouras; Lisa M. DiRocco

(57) ABSTRACT

An animal, e.g., transgenic mouse, in which the MSH4 gene is misexpressed. The animal is useful for screening treatments for a number of conditions. Methods for identifying contraceptive agents are also described.

11 Claims, 7 Drawing Sheets

Fig. 5A
Fig. 5B
Fig. 5C
Fig. 5D
Fig. 5E
Fig. 5F
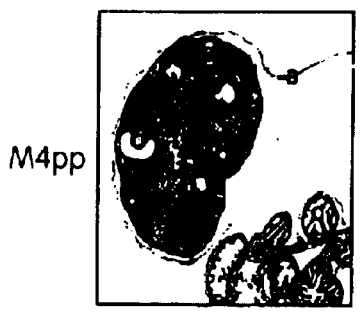
Fig. 5G
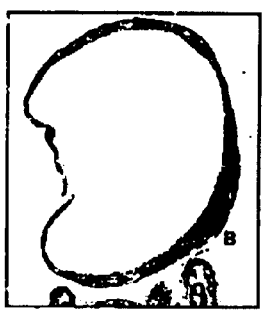
Fig. 5H.1
Fig. 5H.2

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primers

<400> SEQUENCE: 1
tggaaggatt ggagctacgg                                                    20

<210> SEQ ID NO 2
<211> LENGTH: 20
<212> TYPE: DNA
<213> ORGANISM: Artificial Sequence
<220> FEATURE:
<223> OTHER INFORMATION: Primers

<400> SEQUENCE: 2
gaaagcagct gctccgtatc                                                    20
```

METHODS FOR IDENTIFYING CONTRACEPTIVE COMPOUNDS

RELATED APPLICATIONS

This application claims priority to U.S. Provisional Application No. 60/252,661, filed on Nov. 22, 2000, the entire contents of which are incorporated herein by this reference.

GOVERNMENT FUNDING

Work described herein was supported by funding from the National Institute of Health. The United States Government has certain rights to this invention.

FIELD OF THE INVENTION

The invention relates to animals in which the MutS homolog 4 (MSH4) gene is misexpressed and methods of using such animals or cells derived therefrom, e.g., in methods of evaluating fertility treatments.

BACKGROUND OF THE INVENTION

The DNA mismatch repair system (MMR) in mammalian cells is responsible for the repair of DNA mismatches that can result from a number of different mechanisms including DNA replication, genetic recombination and chemical modification of DNA or nucleotide pools. Studies in yeast, and more recently in mice, have also revealed a role for M proteins in the control of meiotic recombination. The bacterial DNA mismatch repair system typified by the *E. coli* Mut HLS system is the simplest and best understood. This system is capable of repairing both single nucleotide mismatches as well as small insertion/deletion mismatches (Kolodner, R. (1996) *Genes Dev* 10: 1433–1442, Modrich, P. et al. (1996) *Annu Rev Biochem* 65: 101-133). In *E. coli*, the Mut S protein recognizes and binds to mismatched nucleotides. In a subsequent step a second protein, Mut L, interacts with Mut S and activates a third protein, Mut H, which is an endonuclease. Mut H nicks the unmethylated strand of hemimethylated DNA in the vicinity of a mismatch, thereby directing the repair of the newly synthesized strand.

While the essential components of this MMR system have been conserved in eukaryotes, the repair system is more complex than in *E. coli* and involves several Mut S and Mut L homologs. In yeast *Saccharomyces cerevisiae* there are six homologs of the DNA binding protein Mut S designated Mut S homolog (MSH) 1–6. There are also four known homologs of the Mut L gene in yeast, designated MLH1, MLH2, PMS1 and MLH3 (Kolodner, R. (1996) *Genes Dev* 10: 1433–1442, Crouse, G. F. (1998) *InDNA Repair in Prokaryotes and Lower Eukaryotes* pp. 411–448). The mammalian genome has homologs for all of these genes except MSH1 which, if present, is yet to be discovered (Buermeyer, A. B., et al (1999) *Annu. Rev. Genet*. 33: 533–564, Kolodner, R. (1996) *Genes Dev* 10: 1433–1442).

It is well established that in eularyotes the products of the MSH2, MSH3, MSH6, as well as MLH1, PMS1 and MLH3 genes are involved in DNA mismatch repair. In eukaryotes, MMR requires a complex of MSH2–MSH6 for the repair of single base mispairs and either a complex of MSH2–MSH6 or MSH2–MSH3 for the repair of insertion/deletion mispairs (Acharya, S. et al. (1996) *Proc Natl Acad Sci USA* 93: 13629–13634, Marsischky, G. T. et al. (1996) *Genes Dev* 10: 407–420, Genschel, J. et al. (1998) *J Biol Chem* 273: 19895–19901, Guerrette, S., et al. (1998) *Mol Cell Biol* 18: 6616–6623, Umar, A. et al. (1998) *Genetics* 148: 1637–1646). The two MSH complexes interact with the complexes of MLH1-PMS1 (PMS2 in human) or MLH1-MLH3 for the repair of the different mismatches (Prolla, T. A. et al. (1998) *Nat Genet* 18: 276–279, Li, G. M. et al. (1995) *Proc Natl Acad Sci USA* 92: 1950–1954, Habraken, Y. et al. (1997) *Curr Biol* 7: 790–793, Pang, Q. et al. (1997) *Mol Cell Biol* 17: 4465–4473, Flores-Rozas, H. et al. (1998) *Proc Natl Acad Sci USA* 95: 12404–12409, Wang, T. F. et al. (1999) *Proc Natl Acad Sci USA* 96: 13914–13919).

Germ line mutations in some of the MMR genes in humans are associated with the cancer predisposition syndrome, hereditary non-polyposis colon cancer (HNPCC). This syndrome is inherited in an autosomal dominant fashion and is characterized by a predispostion to develop colonic and extracolonic tumors where the tumors have a characteristic replication error (RER$^+$) phenotype (Kinzler, K. W. et al. (1996) *Cell* 87: 159–170). Germ-line mutations in MSH2 and MLH1 account for a majority of HNPCC families (Peltomaki, P. et al. (1997) *Gastroenterology* 113: 1146–1158). Recently it is was found that MSH6 germ-line mutations account for a small number of HNPCC families but appear to be also responsible for a larger number of late-onset familial colorectal cancer cases (Wu, Y. et al. (1999) *Am J Hum Genet* 65: 1291–1298).

Studies in bacteria and yeast showed that the MMR system is also involved in the control of recombination. For example, genetic analysis in yeast showed that the complexes consisting of the MMR proteins MSH2–MSH6, MSH2–MSH3, and MLH1-PMS1 function in the prevention of recombination between divergent DNA sequences. This role in recombination is dependent on interactions with other proteins including RAD1–RAD10 and EXO1 (Nakagawa, T. et al. (1999) *Proc Natl Acad Sci USA* 96: 14186–14188). Two other members of the yeast MSH family, MSH4 and MSH5, play a role specifically in meiotic recombination. Yeast strains carrying null mutations in either MSH4 or MSH5 show reduced rates of crossing over but not gene conversion, increased chromosomal nondisjunction and reduced spore viability (Ross-Macdonald, P. et al. (1994) *Cell* 79: 1069–1080, Hollingsworth, N. M. et al. (1995) *Genes Dev* 9: 1728–1739). The analysis of MSH4/MSH5 double mutant yeast strains indicates that MSH4 and MSH5 function in the same genetic pathway with MSH5 being epistatic to MSH4 (Hollingsworth, N. M. et al. (1995) *Genes Dev* 9: 1728–1739). Yeast MSH4 and MSH5 are able to form heterodimeric complexes similar to the mitotic MSH proteins (Pochart, P., D. et al. (1997) *J Biol Chem* 272: 30345–30349). In a manner analogous to mitotic MMR, the analysis of MSH4/MLH1 double mutant yeast strains indicated that the meiosis specific MutS homologs require the function of MLH1 for the promotion of meiotic crossing-over (Hunter, N. et al. (1997) *Genes Dev* 11: 1573–1582).

To understand the role of the mammalian mismatch repair genes in DNA repair, cancer predisposition and meiosis, several mouse lines with targeted mutations in MMR genes have been generated. Mice that carry mutations in the mismatch repair genes Msh2 (de Wind et al. (1995) *Cell* 82:321–330; Reitmair et al. (1995) *Nat Genet* 11:64–70), Msh3 (de Wind et al. (1999) *Nat Genet* 23:359–362; Edelmann et al. (2000) *Cancer Res* 60:803–807), Msh6 (Edelmann et al. (1997) *Cell* 91:467–477), Mlh1 (Baker et al. (1996) *Nat Genet* 13:336–342; Edelmann et al. (1996) *Cell* 85:1125–1134), Pms2 (Baker et al. (1995) *Cell* 82:309–319) and *Pms*1 (Prolla et al. (1998) *Nat Genet* 18:276–279) have been described. Msh2$^{-/-}$, Mlh1$^{-/-}$, Msh6$^{-/-}$ and Pms2$^{-/-}$ mice display a predisposition to tumors, although the degree of this predisposition and the latency for tumor development differ. Mice lacking Msh3 and Pms1 are reported to be normal.

Mice that are homozygous for mutations in the somatic members of the MSH gene family (Msh2, Msh3 and Msh6), are viable and fully fertile (de Wind et al. (1995) *Cell* 82:321–330; Reitmair et al. (1995) *Nat Genet* 11:64–70; Edelmann et al. (1997) *Cell* 25 91:467–477); Edelmann et al. (2000) *Cancer Res* 60:803–807). However, mice that are mutant for the mutL homologs Pms2 and Mlh1 also exhibit a meiotic defect in addition to their cancer predisposition phenotypes. Male mice bearing a homozygous mutation in Pms2 show abnormal chromosome pairing during meiosis and are sterile while the females are fertile (Baker et al. (1995) *Cell* 82:309–319). Mice with mutations in the Mlh1 gene are viable but both sexes are sterile. In spermatocytes from Mlh1 mutant males normal chromosome pairing was observed in pachynema of prophase I, but most of the cells fail to progress beyond pachynema (Baker et al. (1996) *Nat Genet* 13:336–342; Edelmann et al. (1996) *Cell* 85: 1125–1134).

The observation that mutations in the mutL homologous genes result in a different meiotic phenotype compared to mutations in the mutS homologous genes with which they interact during mitotic DNA mismatch repair indicates that the MLH proteins employ different members of the MSH family as partners during meiosis. Recently the human homologs of the yeast MSH4 and MSH5 genes have been isolated and their expression in human germ cells (Paquis-Flucklinger et al. (1997) *Genomics* 44:188–194; Her C. et al. (1998) *Genomics* 52:50–61; Winand et al. (1998) *Genomics* 53:69–80) suggests that one or both of these gene products may be partners for MLH1 during meiosis. Indeed Msh5 mutant mice are viable but both males and females are sterile. Meiosis in these mice cannot progress normally because chromosome pairing is severely affected during prophase I (de Vries et al. (1999) *Genes Dev* 13:523–531; Edelmann et al. (1999) *Nat Genet* 21:123–127).

SUMMARY OF THE INVENTION

The present invention is based, at least in part, on the generation of animals which are homozygous for a null mutation in the MutS homolog 4 (MSH4) gene and the observation that MSH4 is required for normal chromosome pairing during prophase I. The present invention is further based, at least in part, on the discovery that MSH4 and MSH5 are both essential for proper chromosome pairing during mammalian meiosis and that they act in the same pathway.

Accordingly, the invention features a non-human animal in which the gene encoding the MutS homolog 4 (MSH4) protein is misexpressed.

In preferred embodiments the animal, which is preferably a transgenic animal, is a mammal, e.g., a non human primate or a swine, e.g., a miniature swine, a monkey, a goat, or a rodent, e.g., a rat, but preferably a mouse.

In preferred embodiments, expression of the gene encoding the MSH4 protein is decreased as compared to the wild-type animal. For example, the levels of the MSH4 protein can be suppressed by, at least, 50%, 60%, 70%, 80%, 90%, or 100% as compared to the wild-type animal.

In preferred embodiments, misexpression of the gene encoding the MSH4 protein is caused by disruption of the MSH4 gene. For example, the MSH4 gene can be disrupted through removal of DNA encoding all or part of the protein.

In preferred embodiments, the animal can be heterozygous or homozygous for a misexpressed MSH4 gene, e.g., it can be a transgenic animal heterozygous or homozygous for an MSH4 transgene.

In preferred embodiments, the animal is a transgenic mouse with a transgenic disruption of the MSH4 gene, preferably an insertion or deletion, which inactivates the gene product.

In another aspect, the invention features a nucleic acid molecule which, when introduced into an animal or cell, results in the misexpression of the MSH4 gene in the animal or cell. In preferred embodiments, the nucleic acid molecule, includes an MSH4 nucleotide sequence which includes a disruption, e.g., an insertion or deletion, and preferably the insertion of a marker sequence. For example, a nucleic acid molecule can be the targeting construct shown in FIG. 2.

In another aspect, the invention features a method for identifying a compound that modulates, e.g., inhibits, the interaction between MSH4 and MSH5. The method includes contacting, e.g., directly or indirectly, MSH4 with the compound and determining the ability of the compound to modulate the interaction between MSH4 and MSH5.

In another aspect, the invention features a method for identifying a contraceptive compound. The method includes contacting, e.g., directly or indirectly, MSH4 with a test compound and determining the ability of the test compound to inhibit an activity of MSH4 e.g., the ability of MSH4 to interact with MSH5 or other molecules that function in the same genetic pathway as MSH4, thereby identifying a contraceptive compound.

In another aspect, the invention features a method for effecting contraception in a subject, e.g., a human, by administering to the subject a compound that inhibits an activity of MSH4, e.g., the ability of MSH4 to interact with MSH5 or other molecules that function in the same genetic pathway as MSH4.

In another aspect, the invention features a method for modulating, e.g., inhibiting, meiotic recombination in a cell by contacting the cell with a compound that modulates, e.g., inhibits, an activity of MSH4, such as the interaction between MSH4 and MSH5.

In another aspect, the invention features a method of evaluating a fertility treatment. The method includes administering the treatment to an MSH4 misexpressing animal, e.g., a transgenic mouse, or a cell derived therefrom, and determining the effect of the treatment on a fertility indication, e.g., sperm count, testicular size, or oocyte morphology, to thereby evaluate the treatment for fertility. The method may be performed in vivo or in vitro.

In preferred embodiments, the animal or cell is an animal or cell described herein. In other preferred embodiments, the method uses a transgenic mouse in which the expression of the MSH4 gene is inhibited. In yet other preferred embodiments, the method uses a cell derived from a transgenic mouse in which the expression of the MSH4 gene is inhibited.

In another aspect, the invention features a method for identifying a compound which modulates, e.g., inhibits, an activity of MSH4. The method includes contacting, e.g., directly or indirectly, MSH4 with a test compound and determining the effect of the test compound on an activity of MSH4 to, thereby, identify a compound which modulates an MSH4 activity. In preferred embodiments, the activity of MSH4 is inhibited.

In another aspect, the invention features a method for modulating the activity of MSH4. The method includes contacting, e.g., directly or indirectly, MSH4 or a cell expressing MSH4 with a compound which binds to MSH4 in an amount sufficient (e.g., a sufficient concentration) to modulate the activity of MSH4. In preferred embodiments, the activity of MSH4 is inhibited, e.g., the method can be used in contraception.

In another aspect, the invention features a method of identifying a subject having or at risk of developing a fertility disease or disorder. The method includes obtaining a sample from the subject; contacting the sample with a nucleic acid probe or primer which selectively hybridizes to MSH4 and determining whether aberrant MSH4 expression or activity exists in the sample, thereby, identifying a subject having or at risk of developing a fertility disease or disorder.

In another aspect, the invention features an isolated cell, or a purified preparation of cells, from an MSH4 misexpressing animal, e.g., an MSH4 misexpressing animal described herein. In preferred embodiments, the cell is a transgenic cell, in which the gene encoding the MSH4 protein is misexpressed. The cell, preferably a transgenic cell, can be an oocyte or a spermatocyte. In preferred embodiments, the cell is heterozygous or homozygous for the transgenic mutant gene.

Other features and advantages of the invention will be apparent from the following detailed description, and from the claims.

BRIEF DESCRIPTION OF THE DRAWINGS

FIG. 5 depicts a histological analysis of neonatal and adult ovaries from Msh4$^{+/+}$ and Msh4$^{-/-}$ females. Neonatal ovaries at e18 (A, B), day 2 pp (C, D) and day 4 pp (E, F) were stained with anti-GCNA1 antibody (red precipitate). GCNA1 is localized to oogonia and oocytes entering the initial stages of meiosis I, and is then lost as oocytes enter dictyate arrest prior to metaphase I. Oocytes in dictyate arrest are indicated by arrows in panel C and E (PF, primordial follicles). Scale bars=100 µm. (G, H) Adult ovaries at 4 months pp were stained with hematoxylin and eosin. Adult Msh4$^{-/-}$ ovaries from the same animal frequently showed strikingly different phenotypes (Hi, Hii).B, ovarian bursa; Ov, oviduct.

DETAILED DESCRIPTION

Figure 1A:
FIG. 1 depicts the localization of MSH4 on meiotic chromosomes during prophase I. Panels A–D depict the results from the immunofluorescent co-localization of MSH4 (red) and the synaptonemal complex protein, COR1 (white) on chromosome spreads from wild-type spermatocytes at day 17 pp [(A) Leptonema, (B) zygonema, (C) early pachynema and (D) mid pachynema]. Panel E is a graph depicting the quantitation of foci associated with meiotic chromosomes during prophase I (mean±sd). Solid bars represent mean number of foci associated with the COR1 protein at each stage of prophase I, while empty bars represent the number of foci observed throughout the nucleus. One way an ova reveals a high degree of significance across the stages (p<0.0001). Asterixes indicate statistically significant differences from both leptotene foci (on chromosomes) and mid-pachytene foci (Dunn's multiple post test, p<0.001, n=12 nuclei per genotype).

The present invention is based, at least in part, on the generation of animals which are homozygous for a null mutation in the MutS homolog 4 (MSH4) gene and the observation that these animals are sterile. As shown in the Examples, MSH4 has an essential role in the control of male and female meiosis. MSH4 is present in the nuclei of spermatocytes early in prophase I and forms discrete foci along meiotic chromosomes during the zygotene and pachytene stages of meiosis. Disruption of the MSH4 gene in mice resulted in male and female sterility due to meiotic failure. While meiosis was initiated in MSH4 mutant male and female mice, as indicated by the chromosomal localization of RAD51 and COR1 during leptonema/zygonema, the chromosomes failed to undergo normal pairing. As also demonstrated in the Examples presented herein, MSH4 localization on chromosomes during the early stages of meiosis is essential for normal chromosome synapsis in propbase I and acts in the same pathway as MSH5.

Accordingly, the invention features a non-human animal, in which the gene encoding the MutS homolog 4 (MSH4) protein is misexpressed. In preferred embodiments the animal is a transgenic animal.

As used herein, a "transgenic animal" includes an animal, e.g., a non-human mammal, e.g., a swine, a monkey, a goat, or a rodent, e.g., a mouse, in which one or more, and preferably essentially all, of the cells of the animal include a transgene. The transgene is introduced into the cell, directly or indirectly by introduction into a precursor of the cell, e.g., by microinjection, transfection or infection, e.g., by infection with a recombinant virus. The term genetic manipulation includes the introduction of a recombinant DNA molecule. This molecule may be integrated within a chromosome, or it may be extrachromosomally replicating DNA.

As used herein, the term "rodent" includes all members of the phylogenetic order Rodentia.

As used herein, the term "misexpression" includes a non-wild type pattern of gene expression. Expression as used herein includes transcriptional, post transcriptional, e.g., mRNA stability, translational, and post translational stages. Misexpression includes expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-translational modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. Misexpression includes any expression from a transgenic nucleic acid. Misexpression includes the lack or nonexpression of a gene or transgene, e.g., that can be induced by a deletion of all or part of the gene or its control sequences.

As used herein, the term "knockout" includes an animal or cell derived therefrom, in which the insertion of a transgene disrupts an endogenous gene in the animal or cell derived therefrom. This disruption can essentially eliminate MSH4 in the animal or cell.

In preferred embodiments, misexpression of the gene encoding the MSH4 protein is caused by disruption of the MSH4 gene. For example, the MSH4 gene can be disrupted through removal of DNA encoding all or part of the protein.

In preferred embodiments, the animal can be heterozygous or homozygous for a misexpressed MSH4 gene, e.g., it can be a transgenic animal heterozygous or homozygous for an MSH4 transgene.

In preferred embodiments, the animal is a transgenic mouse with a transgenic disruption of the MSH4 gene, preferably an insertion or deletion, which inactivates the gene product.

In another aspect, the invention features a nucleic acid molecule which, when introduced into an animal or cell, results in the misexpression of the MSH4 gene in the animal or cell. In preferred embodiments, the nucleic acid molecule, includes an MSH4 nucleotide sequence which includes a disruption, e.g., an insertion or deletion, and preferably the insertion of a marker sequence. The nucleotide sequence of the wild type MSH4 is known in the art and described in, for example, Paguis-Flucklinger V. et al (1997) *Genomics* 44(2) :188–94, the contents of which are incorporated herein by reference. For example, the nucleic acid molecule can be the targeting construct, shown in FIG. 2.

As used herein, the term "marker sequence" includes a nucleic acid molecule that (a) is used as part of a nucleic acid construct (e.g., the targeting construct) to disrupt the expression of the gene of interest (e.g., the MSH4 gene) and (b) is used to identify those cells that have incorporated the targeting construct into their genome. For example, the marker sequence can be a sequence encoding a protein which confers a detectable trait on the cell, such as an antibiotic resistance gene, e.g., a neomycin resistance gene, or an assayable enzyme not typically found in the cell, e.g., alkaline phosphatase, horseradish peroxidase, luciferase, beta-galactosidase and the like.

As used herein, "disruption of a gene" includes a change in the gene sequence, e.g., a change in the coding region of the gene. A disruption includes insertions, deletions, point mutations, and rearrangements, e.g., inversions. The disruption can occur in one or more exons and/or in the promoter region of the MSH4 gene so as to decrease or prevent expression of the gene in a cell as compared to the wild-type or naturally occurring sequence of the gene. The "disruption" can be induced by classical random mutation or by site directed methods. Disruptions can be transgenically introduced. The deletion of an entire gene is defined herein as a disruption. Preferred disruptions reduce MSH4 levels to about 50% of wild type, in heterozygotes or essentially eliminate MSH4 in homozygotes.

In another aspect, the invention features a method for identifying a compound that modulates, e.g., inhibits, the interaction between MSH4 and MSH5. The method includes contacting, e.g., directly or indirectly, MSH4 with the compound and determining the ability of the compound to modulate the interaction between MSH4 and MSH5. The methods of the invention can further be used to identify a compound that modulates, e.g., inhibits, the interaction between MSH4 and MLH1, MLH3, or PMS2, respectively.

In another aspect, the invention features a method for identifying a contraceptive compound. The method includes contacting, e.g., directly or indirectly, MSH4 with a test compound and determining the ability of the test compound to inhibit an activity of MSH4, e.g., the ability of MSH4 to interact with MSH5 or other molecules that function in the same genetic pathway as MSH4, thereby identifying a contraceptive compound.

As used herein, a "contraceptive compound" includes a compound capable of preventing fertilization (penetration of an ovum by a spermatozoon and the subsequence union of the sperm nucleus and the nucleus of the ovum), preferably without destroying fertility.

In another aspect, the invention features a method for effecting contraception in a subject, e.g., a human, by administering to the subject a compound that inhibits an activity of MSH4, e.g., the ability of MSH4 to interact with MSH5 or other molecules that function in the same genetic pathway as MSH4. As used herein, the term "subject" is intended to include animals such as mammals, most preferably humans. In a preferred embodiment, the subject is a primate. In an even more preferred embodiment, the primate is a human. Other examples of subjects include monkeys, mice, rats, dogs, cats, goats, sheep, rabbits, and cows. As used herein, the term "contraception" includes the prevention of fertilization, preferably without destroying fertility. As used herein, the term "compound" includes any agent, e.g., peptides, peptidomimetics, small molecules, or other drugs, which bind to MSH4 proteins (directly or indirectly), have a stimulatory or inhibitory effect on, for example, MSH4 expression or MSH4 activity, or have a stimulatory or inhibitory effect on, for example, the expression or activity of an MSH4 substrate, e.g., MSH5, MLH1, MLH3, or PMS2.

In another aspect, the invention features a method for modulating, e.g., inhibiting meiotic recombination in a cell by contacting the cell with a compound that modulates, e.g., inhibits, an activity of MSH4, such as the interaction between MSH4 and MSH5. In another aspect, the invention features a method for identifying a compound which modulates the activity of MSH4. The method includes contacting, e.g., directly or indirectly, MSH4 with a test compound and determining the effect of the test compound on the activity of MSH4 to, thereby, identify a compound which modulates MSH4 activity. In preferred embodiments, the activity of MSH4 is inhibited.

In another aspect, the invention features a method for modulating the activity of MSH4. The method includes contacting, e.g., directly or indirectly, MSH4 or a cell expressing MSH4 with a compound which binds to MSH4 in an amount sufficient to modulate the activity of MSH4. In preferred embodiments, the activity of MSH4 is inhibited.

In another aspect, the invention features a method of evaluating a fertility treatment. The method includes administering the treatment to an MSH4 misexpressing animal or a cell derived therefrom; and determining the effect of the treatment on a fertility indication, to thereby evaluate the treatment for fertility. The method may be performed in vivo or in vitro. As used herein, the term "fertility indication" includes any parameter related to fertility, e.g., sperm count, testicular size, or oocyte morphology.

As used herein, "administering a treatment to an animal or cell" is intended to include dispensing, delivering, or applying a treatment to an animal or cell. In terms of the therapeutic agent, e.g., the compounds identified by the methods described herein, the term "administering" is intended to include contacting or dispensing, delivering or applying the therapeutic agent to an animal by any suitable route for delivery of the therapeutic agent to the desired location in the subject. Routes of administration include parenteral routes, in particular intramuscular (i.m.) injection and subcutaneous/intradermal (s.c/i.d.) injection. Alternatively, the therapeutic agent can be administered to the subject orally. Other suitable parental routes include intravenous injection, buccal administration, transdermal delivery and administration by the rectal, vaginal, ophthalmic, intranasal or respiratory tract route.

In preferred embodiments, the animal or cell is an animal or cell described herein. In other preferred embodiments, the method uses a transgenic mouse in which the expression of the MSH4 gene is inhibited. In yet other preferred embodiments, the method uses a cell derived from a transgenic mouse in which the expression of the MSH4 gene is inhibited.

In another sect, the invention features a method of identifying a subject having or at risk of developing a fertility disease or disorder. The method includes obtaining a sample from the subject, contacting the sample with a nucleic acid probe or primer which selectively hybridizes to MSH4 and determining whether aberrant MSH4 expression or activity exists in the sample, thereby identifying a subject having or at risk of developing a fertility disease or disorder.

As used herein, the term "fertility disease or disorder" includes any disease disorder or condition which affects fertilization. Fertility diseases include conditions in which the development of the gametes, ie., the ovum and the sperm, is abnormal, as well as conditions in which a fetus cannot be carried to term. Examples of such fertility disorders include low sperm count, habitual abortion, and abnormal ovulation.

In another aspect, the invention features an isolated cell, or a purified preparation of cells, from an MSH4 misexpressing animal, e.g., an MSH4 misexpressing animal described herein. In preferred embodiments, the cell is a transgenic cell, in which the gene encoding the MSH4 protein is misexpressed. The cell, preferably a transgenic cell, may be an oocyte or a spermatocyte.

In preferred embodiments, the cell is heterozygous or homozygous for the transgenic mutant gene.

As used herein, the term "transgenic cell" includes a cell containing a transgene.

As used herein, "purified preparation" is a preparation which includes at least 10%, more preferably 50%, yet more preferably 90% by number or weight of the subject cells.

The present invention is described in further detail in the following subsections.

Preparation of MSH4 Targeting Constructs

The MSH4 nucleotide sequence to be used in producing the targeting construct is digested with a particular restriction enzyme selected to digest at a location(s) such that a new DNA sequence encoding a marker gene can be inserted in the proper position within this MSH4 nucleotide sequence. The marker gene should be inserted such that it can serve to prevent expression of the native gene. The position will depend on various factors such as the restriction sites in the sequence to be cut, and whether an exon sequence or a promoter sequence, or both is (are) to be interrupted (i.e., the precise location of insertion necessary to inhibit MSH4 gene expression). In some cases, it will be desirable to actually remove a portion or even all of one or more exons of the gene to be suppressed so as to keep the length of the targeting construct comparable to the original genomic sequence when the marker gene is inserted in the targeting construct. In these cases, the genomic DNA is cut with appropriate restriction endonucleases such that a fragment of the proper size can be removed.

The marker sequence can be any nucleotide sequence that is detectable and/or assayable. For example, the marker gene can be an antibiotic resistance gene or other gene whose expression in the genome can easily be detected. The marker gene can be linked to its own promoter or to another strong promoter from any source that will be active in the cell into which it is inserted; or it can be transcribed using the promoter of the MSH4 gene. The marker gene can also have a polyA sequence attached to the 3' end of the gene; this sequence serves to terminate transcription of the gene. For example, the marker sequence can be a protein that (a) conifers resistance to antibiotics or other toxins; e.g., ampicillin, tetracycline, or kanamycin for prokaryotic host cells, and neomycin, hygromycin, or methotrexate for mammalian cells; (b) complements auxotrophic deficiencies of the cell; (c) supplies critical nutrients not available from complex media; or (d) may be detected or viewed by fluorescence.

After the MSH4 DNA sequence has been digested with the appropriate restriction enzymes, the marker gene sequence is ligated into the MSH4 DNA sequence using methods known to the skilled artisan and described in Sambrook et al., *Molecular Cloning A Laboratory Manual*, 2nd Ed., ed., Cold Spring Harbor Laboratory Press: 1989, the contents of which are incorporated herein by reference.

Preferably, the ends of the DNA fragments to be ligated are compatible; this is accomplished by either restricting all fragments with enzymes that generate compatible ends, or by blunting the ends prior to ligation. Blunting is performed using methods known in the art, such as for example by the use of Klenow fragment DNA polymerase I) to fill in sticky ends.

The ligated targeting construct can be inserted directly into embryonic stem cells, or it may first be placed into a suitable vector for amplification prior to insertion. Preferred vectors are those that are rapidly amplified in bacterial cells such as the pbluescript II SK vector (Stratagene, San Diego, Calif.) or pGEM7 (Promega Corp., Madison, Wis.).

The sequences for the mouse and the human MSH4 mRNA are known and may be found as GenBank Accession Numbers AF178957 and XM_001496.5, respectively. There are two general transgenic modificators that may be performed to validate models for contraceptive development. The first involves the conditional ablation of MSH4 by gene targeting. In this, loxP sites are introduced into the mouse genome on either side of an essential coding exon of Msh4 in an intron through homologous recombination. These gene-targeted mice are then crossed with mice expressing cre-recombinase expressed from a specific meiotic gonocyte specific promoter such as Scp1 or ZP3. This will cause ablation of MSH4 in gonocytes at a point beyond which MSH4 first functions. This will test the use of MSH4 at post leptonema stages to establish whether later stages in meiosis than leptonema could be targets for anti–MSH4 pharmacological agents. A second class of construct would be the creation of transgenic mice expressing a dominant negative or gain of function MSH4 molecule driven from a regulatable meiosis specific promoter. This would be best constructed with a tetracycline-on or ecdysome-on system such that the expression of MSH4 could be achieved at a specific stage of meiosis. Possible promoters that could be used would be Cor1, Scp1, ZP3 etc. These transgenic experiments could be used to rescue the Msh4 null mutation at a specific stage of meiosis followed by turn off of the gene in order to test if MSH4 has functions later in meiosis than those already shown in leptonema. Similarly, a dominant negative Msh4 construct could be used to perturb MSH4:MSH5 interactions to provide proof of concept for contraceptives acting at different stages of meiosis.

Construction of Transgenic Mice

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986).

Transfection of Embryonic Stem Cells

Mouse embryonic stem cells (ES cells) can be used to generate the transgenic (e.g., knockout) MSH4 mice. Any ES cell line that is capable of integrating into and becoming part of the germ line of a developing embryo, so as to create germ line transmission of the targeting construct is suitable for use herein. For example, a mouse strain that can be used for production of ES cells, is the 129J strain. A preferred ES cell line is murine cell line D3 (American Type Culture Collection catalog no. CRL 1934). The cells can be cultured and prepared for DNA insertion using methods known in the art and described in Robertson, *Teratocarcinomas and Embryonic Stem Cells: A Practical Approach*, E. J. Robertson, ed. IRL Press, Washington, D.C., 1987, in Bradley et al., *Current Topics in Devel. Biol.*, 20:357–371, 1986 and in Hogan et al., *Manipulating the Mouse Embryo: A Laboratory Manual*, Cold Spring Harbor Laboratory Press, Cold Spring Harbor, N.Y., 1986, the contents of which are incorporated herein by reference.

The knockout construct can be introduced into the ES cells by methods known in the art, e.g., those described in Sambrook et al. Suitable methods include, electroporation, microinjection, and calcium phosphate treatment methods.

The targeting construct to be introduced into the ES cell is preferably linear. Linearization can be accomplished by digesting the DNA with a suitable restriction endonuclease selected to cut only within the vector sequence and not within the MSH4 gene sequence.

After the introduction of the targeting construct, the cells are screened for the presence of the construct. The cells can be screened using a variety of methods. Where the marker gene is an antibiotic resistance gene, the cells can be cultured in the presence of an otherwise lethal concentration of antibiotic. Those cells that survive have presumably integrated the knockout construct. A southern blot of the ES cell genomic DNA can also be used. If the marker gene is a gene that encodes an enzyme whose activity can be detected (e.g., beta-galactosidase), the enzyme substrate can be added to the cells under suitable conditions, and the enzymatic activity can be analyzed.

To identify those cells with proper integration of the targeting construct, the DNA can be extracted from the ES cells using standard methods. The DNA can then be probed on a southern blot with a probe or probes designed to hybridize in a specific pattern to genomic DNA digested with particular restriction enzymes. Alternatively, or additionally, the genomic DNA can be amplified by PCR with probes specifically designed to amplify DNA fragments of a particular size and sequence such that, only those cells containing the targeting construct in the proper position will generate DNA fragments of the proper size.

Injection/Implantation of Embryos

Procedures for embryo manipulation and microinjection are described in, for example, *Manipulating the Mouse Embryo* (Cold Spring Harbor Laboratory Press, Cold Spring Harbor, N.Y., 1986, the contents of which are incorporated herein by reference). Similar methods are used for production of other transgenic animals. In an exemplary embodiment, mouse zygotes are collected from six week old females that have been super ovulated with pregnant mares serum (PMS) followed 48 hours later with human chorionic gonadotropin. Primed females are placed with males and checked for vaginal plugs on the following morning. Pseudo pregnant females are selected for estrus, placed with proved sterile vasectomized males and used as recipients. Zygotes are collected and cumulus cells removed. Furthermore, blastocytes can be harvested. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of an MSH4 targeting construct can be performed using standard micro manipulators attached to a microscope. For instance, embryos are typically held in 100 microliter drops of KSOM under oil while being microinjected. DNA solution is microinjected into the male pronucleus. Successful injection is monitored by swelling of the pronucleus. Recombinant ES cells can be injected into blastocytes, using similar techniques. Immediately after injection embryos are transferred to recipient females, e.g. mature mice mated to vasectomized male mice. In a general protocol recipient females are anesthetized, paralumbar incisions are made to expose the oviducts, and the embryos are transformed into the ampullary region of the oviducts. The body wall is sutured and the skin closed with wound clips.

Retroviral infection can also be used to introduce an MSH4 transgene into a non-human animal. The developing non-human embryo can be cultured in vitro to the blastocyst stage. During this time, the blastomeres can be targets for retroviral infection (Jaenich, R (1976) Proc. Natl. Acad. Sci USA 73, 1260–1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. USA 82, 6927–6931; Van der Putten, et al. (1985) Proc. Natl. Acad. Sci USA 82, 6148–6152). Transfection is easily and efficiently obtained by culturing the blastomeres on a monolayer of virus-producing cells (Van der Putten, supra; Stewart, et al. (1987) EMBO J. 6, 383–388). Alternatively, infection can be performed at a later stage. Virus or virus-producing cells can be injected into the blastocoele (Jahner, D., et al. (1982) Nature 298, 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner, D. et al. (1982) supra).

Screening for the Presence of the Targeting Construct

Transgenic (e.g., knockout) animals can be identified after birth by standard protocols. DNA from tail tissue can be screened for the presence of the targeting construct using southern blots and/or PCR. Offspring that appear to be mosaics are then crossed to each other if they are believed to carry the targeting construct in their germ line to generate homozygous knockout animals. If it is unclear whether the offspring will have germ line transmission, they can be crossed with a parental or other strain and the offspring screened for heterozygosity. The heterozygotes are identified by southern blots and/or PCR amplification of the DNA.

The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed as set forth above.

Other means of identifying and characterizing the knockout offspring are known in the art. For example, northern blots can be used to probe the mRNA for the presence or absence of transcripts encoding either the gene knocked out, the marker gene, or both. In addition, western blots can be used to assess the level of expression of the gene knocked out in various tissues of these offspring by probing the western blot with an antibody against the protein encoded by the gene knocked out (e.g., the MSH4 protein), or an antibody against the marker gene product, where this gene is expressed. Finally, in situ analysis (such as fixing the cells and labeling with antibody) and/or FACS (fluorescence activated cell sorting) analysis of various cells from the offspring can be performed using suitable antibodies to look for the presence or absence of the targeting construct gene product.

Other Transgenic Animals

The transgenic animal used in the methods of the invention can be a mammal; a bird; a reptile or an amphibian. Suitable mammals for uses described herein include: ruminants; ungulates; domesticated mammals; and dairy animals. Preferred animals include: goats, sheep, camels, cows, pigs, horses, oxen, llamas, chickens, geese, and turkeys. Methods for the preparation and use of such animals are known in the art. A protocol for the production of a transgenic pig can be found in White and Yannoutsos, *Current Topics in Complement Research*: 64*th Forum in Immunology*, pp. 88–94; U.S. Pat. No. 5,523,226; U.S. Pat. No. 5,573,933; PCT Application WO93/25071; and PCT Application WO95/04744. A protocol for the production of a transgenic rat can be found in Bader and Ganten, *Clinical and Experimental Pharmacology and Physiology*, Supp. 3:S81–S87, 1996. A protocol for the production of a transgenic cow can be found in U.S. Pat. Nos. 5,741,957; 6,140,552; 5,633,076 and in *Transgenic Animal Technology, A Handbook*, 1994, ed., Carl A. Pinkert, Academic Press, Inc; Wagner, et al. (1984) Theriogenology 21:29–44; Lohse, J. K., et al. (1985) Theriogenology 23:205; and Van Brunt, J. (1988) Bio/Technology 6:1149–1155. A protocol for the production of a transgenic sheep and goats can be found in *Transgenic Animal Technology, A Handbook*, 1994, ed., Carl A. Pinkert, Academic Press, Inc and in WO97/19589 and WO99/58703.

Uses of MSH4 Transgenic Mice

MSH4 misexpressing animals, e.g., mice, or cells derived therefrom can be used to screen treatments for MSH4-related disorders, e.g., fertility disorders. The candidate treatment can be administered over a range of doses to the animal or cell derived therefrom. Efficacy can be assayed at various time points for the effects of the treatment on the disorder being evaluated.

Such treatments can be evaluated by determining the effect of the treatment on a fertility indication. Such parameters include sperm count, testicular size, or oocyte morphology. For example, treatment of a fertility condition includes treatment of ovary degeneration in the animal to, thereby, identify treatments suitable for administration to human subjects.

Methods of the invention can be used to study cells derived from the MSH4 ablated animals in order to define the mechanism of MSH4 function in cell processes, e.g., meiosis. For example, cells can be isolated from MSH4 misexpressing animals and used to identify agents that act downstream from MSH4 in the MSH4 pathway or in independent pathways.

For example, an MSH4 misexpressing animal, as described herein, may be injected with a molecule, e.g., a small molecule, identified using the screening assays described herein as being able to modulate MSH4 activity. Sufficient time is allowed for the molecule to reach its target site and then the animal is evaluated for testicular size, sperm volume, concentration of sperm, or sperm quality. Ultrasonography, as described in U.S. Pat. No. 5,705,749, may be used to evaluate size and echotexture of gonadal and accessory genital structures. Sperm volume, concentration of sperm, or sperm quality may be evaluated as described in U.S. Pat. Nos. 5,434,057; 6,197,940.

One parameter of sperm function that may be tested is the ability to penetrate cervical mucus. This penetration test can be done either in vitro or in vivo. Briefly, in vitro, a commercial kit containing cervical mucus (Tru-Trax, Fertility Technologies, Natick, Mass.), typically bovine cervical mucus, is prepared. Sperm are placed at one end of the track and the distance that sperm have penetrated into the mucus after a given time period is determined. Alternatively, sperm penetration of mucus may be measured in vivo in female subjects. At various times post-coitus, a sample of cervical mucus is removed and examined microscopically for the number of sperm present in the sample. In the post-coital test, improved sperm function is established if more sperm with faster velocity are seen in the mucus sample.

Other assays of sperm function potential include the sperm penetration and hemizona assays. In the sperm penetration assay, the ability of sperm to penetrate into an oocyte is measured. Briefly, commercially available zona free hamster oocytes are used (Fertility Technologies, Natick, Mass.). Hamster oocytes are suitable in this assay for sperm of any species. Capacitated sperm, such as those cultured with bovine serum albumin for 18 hours, are incubated for 3 hours with the hamster oocytes. Following incubation, oocytes are stained with acetolacmoid or equivalent stain and the number of sperm penetrating each oocyte is counted microscopically. A hemizona assay measures the ability of sperm to undergo capacitation and bind to an oocyte. Briefly, in this assay, live normal sperm are incubated in media with bovine serum albumin, which triggers capacitation. Sperm are then incubated with dead oocytes which are surrounded by the zona pellucida, an a cellular coating of oocytes. Capacitated sperm bind to the zona and the number of sperm binding is counted microscopically.

Candidate Treatments

The candidate treatment, which is evaluated using methods described herein, can include: (a) the administration of a therapeutic agent (e.g., a drug, a chemical, an antibody, a protein, a nucleic acid or other substance) to an MSH4 misexpressing animal or cell; (b) the administration of a diet regimen to an MSH4 misexpressing animal; (c) the administration of ionizing radiation to an MSH4 misexpressing animal or cell. Any combination of the aforementioned treatments can be administered to an MSH4 misexpressing animal or cell. The treatment can be administered prior to, simultaneously and/or after the onset of the disorder or condition, for which the candidate treatment is being evaluated. The therapeutic agent can be administered to a MSH4 misexpressing animal, orally, parenterally, or topically.

Predictive/Diagnostic Assays

The present invention also pertains to the field of predictive medicine in which diagnostic and prognostic assays are used for prognostic (predictive) purposes to thereby treat an individual prophylactically. Accordingly, one aspect of the present invention relates to diagnostic assays for determining MSH4 protein and/or nucleic acid expression as well as MSH4 activity, in the context of a biological sample (e.g. blood, serum, cells, tissue) to thereby determine whether a subject is afflicted with or is at risk of developing a disease or disorder associated with aberrant MSH4 expression or activity, e.g., infertility. The invention also provides for prognostic (or predictive) assays for determining whether a subject is at risk of developing a disorder associated with MSH4 protein activity or nucleic acid expression. For example, mutations in an MSH4 gene can be assayed in a biological sample. Such assays can be used for prognostic or predictive purpose to thereby phophylactically treat an individual prior to the onset of a disorder characterized by or associated with MSH4 protein, nucleic acid expression or activity.

In preferred embodiments, the assays include detecting, in a sample of cells from the subject, the presence or absence of a genetic alteration characterized by at least one of an alteration affecting the integrity of a gene encoding a MSH-4-protein, or the mis-expression of the MSH4 gene. For example, such genetic alterations can be detected by ascertaining the existence of at least one of 1) a deletion of one or more nucleotides from a MSH-4 gene; 2) an addition of one or more nucleotides to a MSH-4 gene; 3) a substitution of one or more nucleotides of a MSH4 gene, 4) a chromosomal rearrangement of a MSH-4 gene; 5) an alteration in the level of a messenger RNA transcript of a MSH-4 gene, 6) aberrant modification of a MSH-4 gene, such as of the methylation pattern of the genomic DNA, 7) the presence of a non-wild type splicing pattern of a messenger RNA transcript of a MSH-4 gene, 8) a non-wild type level of a MSH-4-protein, 9) allelic loss of a MSH4 gene, and 10) inappropriate post-translational modification of a MSH-4-protein. As described herein, there are a large number of assay techniques known in the art which can be used for detecting alterations in an MSH-4 gene. A preferred biological sample is a tissue or serum sample isolated by conventional means from a subject, e.g., an ovary tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the MSH-4-gene (see Abravaya et al. (1995) *Nucleic Acids Res*.23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an MSH-4-gene under conditions such that hybridization and amplification of the MSH-4-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an MSH-4 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

Screening Assays

In another aspect, the invention features a method for identifying a compound which modulates the activity of MSH4. The method includes contacting, e.g., directly or indirectly, MSH4 with a test compound and determining the effect of the test compound on the activity of MSH4 to, thereby, identify a compound which modulates MSH4 activity. In preferred embodiments, the activity of MSH4 is inhibited.

To determine whether a test compound modulates MSH4 expression, a cell which expresses MSH4 (e.g., an ovary cell) is contacted with a test compound, and the ability of the test compound to modulate MSH4 expression can be determined by measuring MSH4 MRNA by, e.g., Northern Blotting, quantitative PCR (e.g. Taqman), or in vitro transcriptional assays. To perform an in vitro transcriptional assay, the fill length promoter and enhancer of MSH4 can be linked to a reporter gene such as chloramphenicol acetyltransferase (CAT) or luciferase and introduced into host cells. The same host cells can then be transfected with or contacted with the test compound. The effect of the test compound can be measured by reporter gene activity and comparing it to reporter gene activity in cells which do not contain the test compound. An increase or decrease in reporter gene activity indicates a modulation of MSH4 expression and is, therefore, an indicator of the ability of the test compound to modulate the activity of MSH4.

In another embodiment, the invention features a method for identifying a compound that modulates, e.g., inhibits, the interaction between MSH4 and MSH5. The method includes contacting, e.g., directly or indirectly, MSH4 with the compound and determining the ability of the compound to modulate the interaction between MSH4 and MSH5. The methods of the invention can further be used to identify a compound that modulates, e.g., inhibits, the interaction between MSH4 and MLH1, MLH3, or PMS2, respectively.

For example, yeast cells harboring MSH4 and MSH5 (e.g., those described herein in Example 9) may serve as the starting material for the assay. The yeast cells are grown into fresh growth medium containing test compounds. Following an incubation time, the cells are lysed and the activity of the reporter is measured. Potential modulators of the interaction are those that show the desired deviation from the signal obtained in the absence of test compound.

An alternative yeast two-hybrid assay format involves the use of an inducible promoter to drive the expression of one of the interaction partners. In this format, the assay is initiated by the addition of the inducer, which turns on the expression of one or both of the interaction partners and results in the generation of a signal, which is the target of modulation.

Examples of systems that may be used in the screening assys of the present invention include those described, for example, in U.S. Pat. Nos. 5,580,736 and 5,955,280, the contents of each of which are incorporated by reference.

In another embodiment, the invention features a method for identifying a contraceptive compound. The method includes contacting, e.g. directly or indirectly, MSH4 with a test compound and determining the ability of the test compound to inhibit an activity of MSH4, e.g., the interaction between MSH4 and MSH5, thereby identifying a contraceptive compound.

The test compounds that may be used in the assays described herein can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des*. 12:145).

Examples of methods for the synthesis of molecular libraries can be found in the art, for example in: DeWitt et al. (1993) *Proc. Natl. Acad Sci. U.S.A.* 90:6909; Erb et al. (1994) *Proc. Natl. Acad. Sci. USA* 91:11422; Zuckermann et al. (1994). *J. Med. Chem*. 37:2678; Cho et al. (1993) *Science* 261:1303; Carrell et al. (1994) *Angew. Chem. Int. Ed. Engl*. 33:2059; Carell et al. (1994) *Angew. Chem. Int. Ed. Engl*. 33:2061; and in Gallop et al. (1994) *J. Med. Chem*. 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci*. 87:6378–6382); (Felici (1991) *J. Mol. Biol*. 222:301–310); (Ladner supra.).

In a preferred embodiment, determining the ability of the test compound to bind to or interact with MSH4 can be accomplished by determining the activity of MSH4. For example, the activity of MSH4 can be determined directly by detecting the ability of MSH4 to interact with MSH5 or indirectly by detecting the ability of chromosomes to undergo meiosis, e.g., to undergo normal pairing. Assays for monitoring chromosomal meiosis are well known in the art and are described in, for example, Woltering D. et al. (2000) *Mol. Cell Biol.* 20(18):6646–58; Spyropoulos, B. and Moens, P. B. (1994) *Methods Mol. Biol.* 33:131–139; Counce, S. J. and Meyer, G. F. (1973) *Chromosoma* 44:231–253; and Kneitz et al. (2000) *Genes and Development* 14:1085–1097, the contents of which are incorporated herein by reference. The activity of MSH4 can further be determined by monitoring the induction of a reporter gene (comprising a target-responsive regulatory element operatively linked to a nucleic acid encoding a detectable marker, e.g., chloramphenicol acetyl transferase), or detecting a target-regulated cellular response.

Determining the ability of the MSH4 protein to bind to an MSH4 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In more than one embodiment of the above assay methods of the present invention, it may be desirable to immobilize either MSH4 or the test compound to facilitate separation of complexed from uncomplexed forms of one or both of the proteins, as well as to accommodate automation of the assay. Binding of a test compound to an MSH4 protein, or interaction of an MSH4 protein with a target molecule (e.g., MSH5) in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/MSH4 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or MSH4 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of MSH4 binding or activity determined using standard techniques.

Other techniques for immobilizing proteins on matrices can also be used in the screening assays of the invention. For example, either an MSH4 protein or an MSH4 target molecule (e.g., MSH5) can be immobilized utilizing conjugation of biotin and streptavidin. Biotinylated MSH4 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the MSH4 protein or target molecules but which do not interfere with binding of the MSH4 protein to its target molecule can be derivatized to the wells of the plate, and unbound target or MSH4 protein trapped in the wells by antibody conjugation. Methods for detecting such complexes, in addition to those described above for the GST-immobilized complexes, include immunodetection of complexes using antibodies reactive with the MSH4 protein or target molecule, as well as enzyme-linked assays which rely on detecting an enzymatic activity associated with the MSH4 protein or target molecule.

In another embodiment, modulators of MSH4 expression are identified in a method wherein a cell is contacted with a test compound and the expression of MSH4 mRNA or protein in the cell is determined. The level of expression of MSH4 mRNA or protein in the presence of the test compound is compared to the level of expression of MSH4 mRNA or protein in the absence of the test compound. The test compound can then be identified as a modulator of MSH4 expression based on this comparison. For example, when expression of MSH4 mRNA or protein is greater (statistically significantly greater) in the presence of the test compound than in its absence, the test compound is identified as a stimulator of MSH4 MRNA or protein expression. Alternatively, when expression of MSH4 mRNA or protein is less (statistically significantly less) in the presence of the test compound than in its absence, the test compound is identified as an inhibitor of MSH4 mRNA or protein expression. The level of MSH4 mRNA or protein expression in the cells can be determined by methods described herein for detecting MSH4 mRNA or protein.

The MSH4 proteins can also be used as "bait proteins" in a two-hybrid assay or three-hybrid assay (see, e.g., Fields S. et al. (1994) *Trends Genet.* 10:286–292; Young P. et al. (1992) *Current Biology* 3:408–420; Zervos et al. (1993) *Cell* 72:223–232; Madura et al. (1993) *J. Biol. Chem.* 268:12046–12054; Bartel et al. (1993) *Biotechniques* 14:920–924; and Iwabuchi et al. (1993) *Oncogene* 8:1693–1696), to identify other proteins, which bind to or interact with MSH4 and are involved in MSH4 activity. Such MSH4-binding proteins are also likely to be involved in the control of meiosis by the MSH4 proteins or MSH4 targets (e.g., MSH5) as, for example, downstream elements of the MSH4 genetic pathway. Alternatively, such MSH4-binding proteins are likely to be MSH4 inhibitors.

The two-hybrid system is based on the modular nature of most transcription factors, which consist of separable DNA-binding and activation domains. Briefly, the assay utilizes two different DNA constructs. In one construct, the gene that codes for a MSH4 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a MSH4-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the MSH4 protein.

In another aspect, the invention pertains to a combination of two or more of the assays described herein. For example, a modulating agent can be identified using a cell-based or a cell-flee assay, and the ability of the agent to modulate the activity of the MSH4 protein can be confirmed in vivo, e.g., using an animal such as an animal model for a fertility disorder.

Moreover, an MSH4 modulator identified as described herein (e.g., an antisense MSH4 nucleic acid molecule, an MSH4-specific antibody, or a small molecule) can be used in an animal model to determine the efficacy, toxicity, or side effects of treatment with such a modulator. Alternatively, an MSH4 modulator identified as described herein can be used in an animal model to determine the mechanism of action of such a modulator.

Contraceptive/Therapeutic Methods

Another aspect of the invention pertains to methods of modulating MSH4 expression or activity for therapeutic purposes. Accordingly, in an exemplary embodiment, the modulatory method of the invention involves contacting a cell with MSH4 or a compound that modulates one or more of the activities of the MSH4 protein. A compound that modulates MSH4 protein activity can be a nucleic acid or a protein, a naturally-occurring target molecule of an MSH4 protein, an MSH4 antibody, an MSH4 agonist or antagonist, a peptidomimetic of an MSH4 agonist or antagonist, or other small molecule. In one embodiment, the compound stimulates one or more MSH4 activities. Examples of such stimulatory compounds include an active MSH4 protein and a nucleic acid molecule encoding MSH4 that has been introduced into the cell. In another embodiment, the compound inhibits one or more MSH4 activities. Examples of such inhibitory compounds include antisense MSH4 nucleic acid molecules, ribozymes, anti–MSH4 antibodies, and MSH4 small molecule inhibitors. These modulatory methods can be performed in vitro (e.g., by culturing the cell with the compound) or, alternatively, in vivo (e.g., by administering the compound to a subject). As such, the present invention provides methods of treating a subject afflicted with a disease or disorder characterized by aberrant expression or activity of an MSH4 protein or nucleic acid molecule, e.g., a fertility disorder. In one embodiment, the method involves administering a compound (e.g., a compound identified by a screening assay described herein), or combination of compounds that modulate (e.g., upregulate or downregulate) MSH4 nucleic acid expression or MSH protein activity. In another embodiment, the method involves administering an MSH4 protein or nucleic acid molecule as therapy to compensate for reduced or aberrant MSH4 expression or activity.

Stimulation of MSH4 activity is desirable in situations in which MSH4 is abnormally downregulated and/or in which increased MSH4 activity is likely to have a beneficial effect. For example, stimulation of MSH4 activity is desirable in situations in which a MSH4 is downregulated and/or in which increased MSH4 activity is likely to have a beneficial effect. Likewise, inhibition of MSH4 activity is desirable in situations in which MSH4 is abnormally upregulated and/or in which decreased MSH4 activity is likely to have a beneficial effect (e.g., in contraception).

Thus, the present invention also features a method for effecting contraception in a subject, e.g., a human, by administering to the subject a compound that inhibits an activity of MSH4, e.g., the ability of MSH4 to interact with MSH5 or other molecules that function in the same genetic pathway as MSH4 or the ability of MSH4 to allow normal chromosomal pairing during meiosis. Any of the compounds described above may be used in the contraceptive methods of the invention.

MSH4 or a compound that modulates one or more of the activities of the MSH4 protein (an MSH4 modulator) may be administered to a subject in need thereof in an amount effective to reach the desired effect in the subject.

As used herein, the term "administering" to a subject includes dispensing, delivering or applying MSH4 or an MSH4 modulator to a subject by any suitable route for delivery of the MSH4 protein or an MSH4 modulator to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the term "effective amount" includes an amount effective, at dosages and for periods of time necessary, to achieve the desired result, e.g. sufficient to treat a fertility disorder in a subject. An effective amount of an MSH4 modulator, as defined herein may vary according to factors such as the disease state, age, and weight of the subject, and the ability of the angiogenesis inhibitor compound to elicit a desired response in the subject. Dosage regimens may be adjusted to provide the optimum therapeutic response. An effective amount is also one in which any toxic or detrimental effects (e.g., side effects) of the angiogenesis inhibitor compound are outweighed by the therapeutically beneficial effects.

A therapeutically effective amount of an MSH4 modulator (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an MSH4 modulator can include a single treatment or, preferably, can include a series of treatments. It will also be appreciated that the effective dosage of an MSH4 modulator used for treatment may increase or decrease over the course of a particular treatment.

This invention is further illustrated by the following examples which should not be construed as limiting. The contents of all references, patents and published patent applications cited throughout this application including the Figures and the Sequence Listing are incorporated herein by reference.

EXAMPLES

Materials and Methods

Inactivation of Msh4 in Embryonic Stem Cells

Figure 2A:
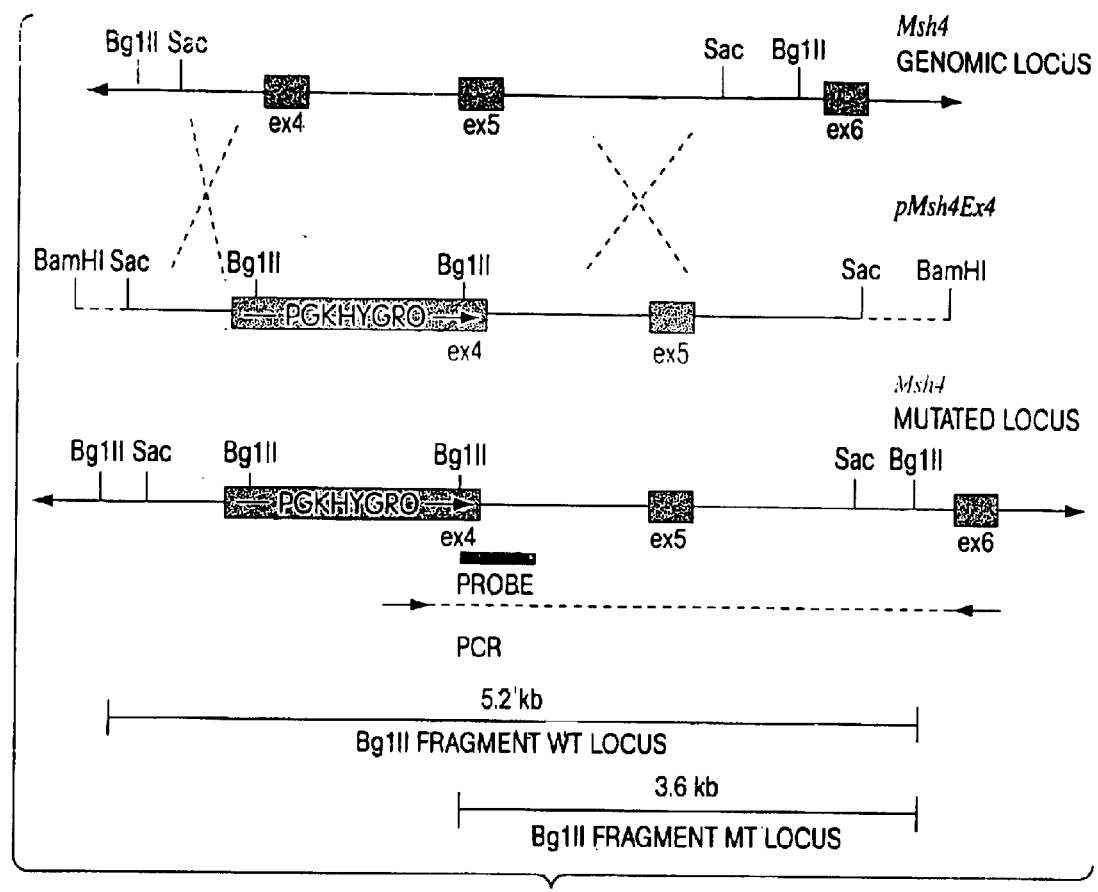
FIG. 2 depicts the gene targeting strategy for the generation of Msh4 mutant mice. Panel A is a schematic representation of the Msh4 wild type gene locus, the pMsh4Ex4 targeting construct and the targeted Msh4 locus. The exons are shown as black boxes. The PCR primers located in the PGKhygromycin cassette and in exon 6 that were used for detecting the gene targeting events are indicated by arrows connected by a dotted line. The diagnostic BglII digestion products for the wild-type Msh4 locus and the modified Msh4 locus that are recognized by the hybridization probe are indicated. Panel B depicts the results from a southern blot hybridization of DNA from mice of the F2 generation. Tail DNA was digested with BglII and hybridized with the probe shown in Panel A. The 5.2 kb band corresponds to the wild-type and the 3.6 kb band corresponds to the targeted allele. (+/+), wild-type; (+/−), heterozygous; (−/−), homozygous. Panel C depicts the detection of Msh4 by Northern blot analysis. Testis poly (A) RNA of the different genotypes was analyzed with a cDNA probe corresponding to the entire Msh4 coding sequence. A human P-actin-specific probe was used as a control. (+/+), wild-type; (+/−), heterozygous; (−/−), homozygous. Panel D depicts the detection of MSH4 protein on meiotic chromosomes. Immunoflourescent co-localization of MSH4 (red) and the synaptonemal complex protein COR1 (white) on chromosome spreads of spermatocytes from day 20 old males. (+/+), chromosome spread from wild-type spermatocytes; (−/−), chromosome spread from homozygous mutant spermatocytes.

A 4.1 kb Sac genomic fragment containing Msh4 exons 4, and 5 derived from a 129Ola lambda phage library was subcloned into pUC19. Comparison of the mouse and human sequences spanning exons 4 and 5 revealed 90% homology between the two species. A single BglII site was inserted into Exon 4 corresponding to human codon 252 by site directed mutagenesis. A 2.0 kb BglII fragment containing PGKhygromycin was cloned into exon 4 in the same transcriptional orientation as the Msh4 gene and the resulting targeting vector was designated pMsh4Ex4. The targeting vector (40 μg) was linearized at the single BamHI side and electroporated into 2.0×10⁷ WW6 ES cells as described in (Edelmann, W., K. et al. (1997) *Cell* 91: 467477). The ES cells were selected in hygromycinB (150 μg/ml) and resistant colonies were isolated after 10 days of selection. Genomic DNA from individual colonies was subjected to Long Range PCR analysis (Boehringer Mannheim) and positive ES cell colonies were identified by a 4.3 kb PCR fragment using forward primer 5'-TGGAAGGATTGGAGCTACGG-3' (SEQ ID NO:1) and reverse primer 5'-GAAAGCAGCTGCTCCGTATC-3' (SEQ ID NO:2). The PCR reactions were performed according to the manufacturers instructions. For Southern blot analysis genomic DNA was digested with BglII, transferred to nylon membrane and hybridized to a genomic probe corresponding to intron 4 (FIG. 2A).

Generation of Msh4$^{-/-}$ Mice

Embryonic stem cells derived from three independently targeted clones were injected into C57B1/6 blastocysts. All three cell lines gave raise to male chimeric animals that were mated to C57B1/6 females. Chimeric males derived from all three cell lines transmitted the mutation through their germ line. F1 heterozygous animals were intercrossed to obtain Msh4 homozygous mutant animals.

Northern Blot Analysis

Mouse multiple tissue Northern blots (Origene) were hybridized with a full length human cDNA probe to determine Msh4 expression. For analysis of Msh4 expression in 23 day old male testis poly (A) RNA was separated on 1.0% agarose formaldehyde gels and transferred to nitrocellulose membranes. For hybridization a human cDNA probe spanning the entire MSH4 coding region and a human β-actin probe was used.

Histology

For analysis of the first meiotic wave in the testis, Msh4$^{+/+}$ and Msh4$^{-/-}$ males were taken between day 17 pp and day 23 pp, corresponding to the end of meiosis I and meiosis II, respectively. Adult males were used at between 10 and 14 weeks of age. For analysis of female meiosis, embryos were taken between e16 and e19 and at day 1 through to day 5 pp. Older females were also used at day 25 pp and adulthood (4 weeks to 7 months of age). For histological analysis, ovaries and testes were fixed in Bouins fixative or 4% buffered formalin for periods of 1 hour until 12 hours, depending on the size of the specimen. Fixed tissues were processed for immunohistochemistry by routine methods and the paraffin-embedded tissues were sectioned at 3–5 μm, depending on the tissue.

Chromosome Analysis

Testes were removed from mice between the ages of day 17 pp and day 25 pp, decapsulated and rinsed in α-MEM. Tubules were chopped coarsely on dental wax and then more finely with watchmakers forceps. Large clumps were removed and the supernatant was centrifuged to pellet the germ cells, which were the resuspended in 20 μl of fresh α-MEM. Aliquots of 4 μl were then applied to a 400 μl bubble of hypotonic (0.5%) saline on parafilm to burst open the cells and to spread the nuclear contents across the concave surface of the bubble. Spread nuclei were then picked up on pre-cleaned slides or on to formvar-coated 200 mesh nickel electron microscopy grids. The nuclei were then fixed twice in 1% paraformaldehyde (pH 8.2) for 3 minutes each on ice, followed by three 1-minute washes in 0.4% photoflo-200 (Kodak). Fixed nuclei were air dried overnight and then used immediately or stored at −70° C. for up to 3 weeks. Nuclei were subjected to either silver staining in 50% AgNO₃ at 55° C. for 1 hour, or used for immunofluorescent analysis of chromosome-associated proteins (see below).

For analysis of female meiotic chromosomes, embryonic ovaries were removed between e16 and e19 and minced finely in cold α-MEM on pre-cleaned microscope slides. Cell suspensions were then applied to a small bubble of hypotonic (0.5%) saline on a clean microscope slide, stirred gently, and then rested for 3 hours to allow the germ cell nuclei to sink through the saline and adhere to the slide. Fixation procedures were the same as for male germ cells above. Slides were used for immunofluorescence as described below.

Immunofluorescence and Immunohistochemistry

Slides containing chromosome spreads were subjected to imnmunofluorescent staining as previously described (Edelmann et al, 1999). Primary antibodies used were: (1) a mouse monoclonal antibody against COR1, a component of the mouse synaptonemal complex (1:1000); (2) a rabbit polyclonal antibody directed against the last 12 amino-acids of mouse MSH4 (1:400) and (3) a rabbit polyclonal antibody raised against mouse RAD51 (1:500).

Paraffin sections were subjected to immunohistochemistry using a rat hybridoma supernatant against germ cell nuclear antigen-1 (GCNA-1) (Enders and May 1994). Alternatively, slides were stained with hematoxylin and eosin to reveal more detailed histological architecture.

Example 1

Association of MSH4 with Meiotic Chromosomes

Figure 1B:
Figure 1C:
Figure 1D:
Figure 1E:
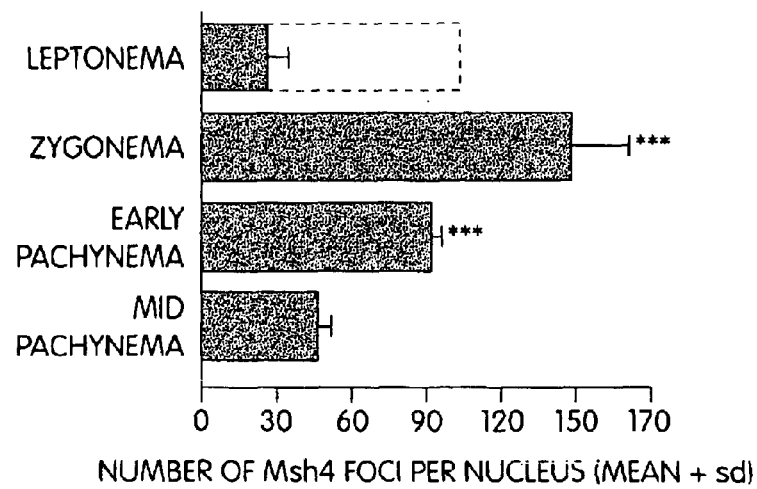

To determine the tissue specific expression pattern of Msh4 Northern blot analysis was performed using a cDNA probe spanning the entire coding region of human MSH4 gene (Paquis-Flucklinger, V., S. et al. (1997) *Genomics* 44: 188–194). A 3.2 kb mRNA transcript was detected in testis but was virtually absent in all other tissues tested including skin, lung, liver, thymus, spleen, brain, heart, kidney, stomach, small intestine and skeletal muscle. The testis specific expression of Msh4 suggested a role similar to its yeast counterpart in the control of meiotic processes. To further investigate this possibility, the distribution of MSH⁴ protein along meiotic chromosomes was analyzed by immunofluorescent methods. The MSH4 protein colocalized with the synaptonemal complex and axial element protein, COR1, on chromosome spreads prepared from wild-type testes at day 17 pp. MSH4 foci were found to be colocalized with the SC from leptonema up until pachynema (FIG. 1). At leptonema, MSH4 was localized throughout the nuclear region, though not intimately associated with the axial element backbone of unsynapsed chromosomes (FIG. 1A, E). By zygonema, MSH4 staining was associated directly with the axial elements themselves, being distributed along much of the length of the meiotic chromosomes. The foci at this stage were of variable size but were still quantifiable (142±24.7 per nucleus: FIGS. 1B, E). Early in pachynema, MSH4 was still present in discrete foci along the SC of synapsed chromosomes, with the number of foci per bivalent remaining high (90±4.5 per nucleus: FIGS. 1C, E). By mid-pachynema the number of MSH4 foci declined further, with an average of 47±4.5 foci per nucleus (FIGS. 1D, E).

Example 2

Generation of Msh4 Mutant Mice

Figure 2B:
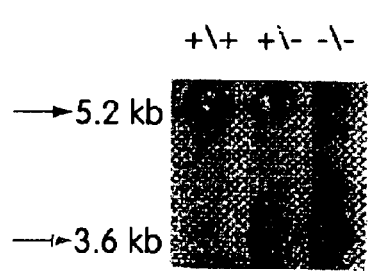

The localization of MSH4 on meiotic chromosomes supported a role for this protein in meiosis. To determine the importance of MSH4 for mammalian meiosis we generated a mouse line that carries an inactivating mutation in the germ line. The gene targeting vector pMsh4ex4 was designed to introduce a PGK hygromycin resistance cassette into exon 4 corresponding to codon 252 of the human MSH4 cDNA (FIG. 2A). This modification introduces multiple stop codons into the Msh4 reading frame as verified by sequencing and is predicted to result in an inactivating mutation. A truncated protein if, produced by the modified Msh4 locus, would lack the nucleotide binding domain and the helix-loop-helix domain located at the COOH-end that are essential for the function of the MutS family of proteins (Ross-Macdonald, P. et al. (1994) *Cell* 79: 1069–1080, Paquis-Flucklinger, V., S. et al.(1997) *Genomics* 44:188–194). The targeting vector pMsh4ex4 was linearized and electroporated into ES cells. 196 hygromycin resistant clones were isolated and screened for the homologous recombination event by PCR (FIG. 2A). Forty-three (22%) of the analyzed clones tested positive for the correct targeting event. The appropriate modification was verified by Southern blot analysis (FIG. 2B). Three independently derived Msh4 ES clones were injected into C57/B16 blastocysts. Chimeric animals from all three cell lines transmitted the disrupted allele through the germ line. Heterozygous F1 animals were interbred to obtain homozygous mutant mice. 518 F2 offspring animals were obtained from 11 mating pairs. Genotyping of the F2 mice revealed that 139 animals were wild type, 263 animals were heterozygous and 116 animals were homozygous for the mutant allele. This result is consistent with a normal Mendelian pattern of inheritance and indicates that MSH4 is not essential for normal development.

Example 3

Characterization of Msh4 Mutant Mice

Lack of Msh4 Transcripts or MSH4 Protein in Testis of Msh4$^{-/-}$ Mice

Figure 2C:
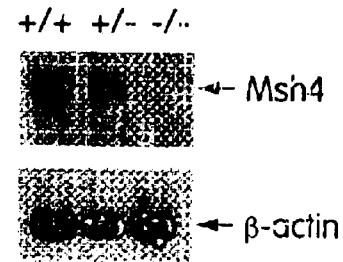
Figure 2D:
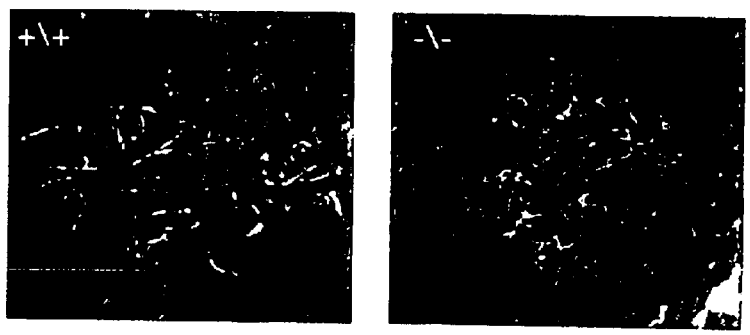

Two lines of evidence indicated that the insertion of the PGK hygromycin cassette into exon 4 resulted in an inactivating mutation. First, to confirm that Msh4$^{-/-}$ mice did not produce normal transcripts testis polyA RNA was subjected to Northern blot analysis (FIG. 2C). The RNA from wild type mice contained a 3.2 kb transcript that was also present at reduced level in heterozygous mice. No Msh4 transcript was detectable in the testis RNA of homozygous mutant mice. Second, the inactivation of MSH4 in homozygous mutant mice was further confirmed by immunolocalization experiments. While MSH4 foci are readily detectable in maximal numbers on wild-type spermatocyte chromosomes at zygonema, no MSH4 protein was present on or around the meiotic chromosomes of Msh4$^{-/-}$ mice at the comparable stage of meiosis (FIG. 2D).

MSH4 Expression in Meiotic Nuclei

Analysis of MSH4 expression in meiotic nuclei revealed that MSH4 is present at the various stages of male prophase I. Early in meiosis during the leptotene stage of prophase I, MSH4 protein accumulated within the nuclear matrix. Subsequently, in zygonema, MSH4 colocalized with the synaptonemal complex protein COR1 and was found at multiple sites along unpaired meiotic chromosomes. The number of these MSH4 foci decreased until mid pachynema to around 47 foci per nucleus, a figure that represents almost twice the number of estimated recombination sites found in mouse spermatocytes at diplonema (27 per nucleus; (Polani, P. E. et al. (1976) *Cytogenetics and Cell Genetics* 16: 505–529)). Tis numerical and temporal correlation between MSH4 foci and chiasmata frequency indicates a specific functional relationship between the two phenomena. The formation of MSH4 foci on zygotene chromosomes in mice differs from that seen in yeast where MSH4 only localizes at discrete locations along synapsed chromosomes during pachynema (Ross-Macdonald, P. et al. (1994) *Cell* 79: 1069–1080). This temporal difference in binding indicates different roles of MSH4 during recombination in yeast and mammals.

Fertility of Msh4$^{-/-}$ Male Mice

Figure 3A:
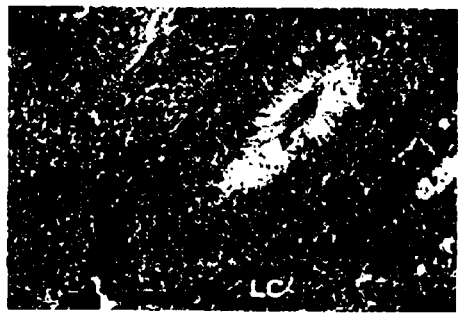
FIG. 3 shows the testis morphology in Msh4$^{+/+}$ and Msh4$^{-/-}$ males. Panels A, C, and E represent testis morphology in wild-type males. Panels B, D, and F represent testis morphology in Msh4$^{-/-}$ mutant males. Hematoxylin and eosin staining (A, B) and immunohistochemical localization of GCNA1-positive spermatogonia and spermatocytes (C, D) in sections of adult testis. (E, F) GCNA1 localization of spermatogonia and spermatocytes at the end of the first wave of prophase I at day 23 pp. LC, Leydig cells. Arrowheads show mature spermatozoa within the lumen of testes from wild-type adult males. Scale bars=200 µm.
Figure 3B:
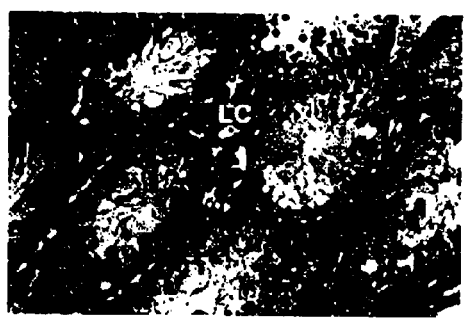
Figure 3C:
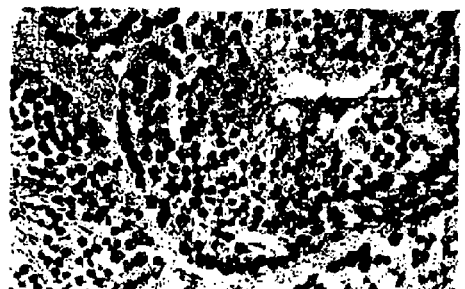
Figure 3D:
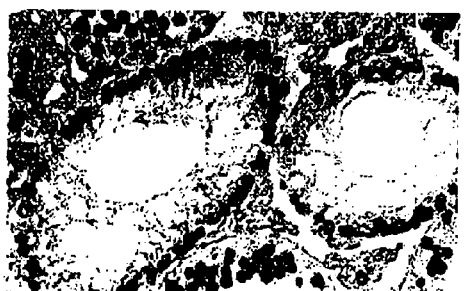
Figure 3E:
Figure 3F:
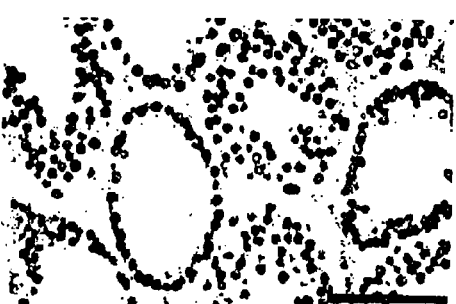

Msh4 mutant animals up to 12 months of age appeared to develop normally without any discernable disease phenotype. However, while Msh4$^{+/+}$ and Msh4$^{+/-}$ males were fertile, matings between Msh4$^{-/-}$ males and wild-type females did not produce any offspring. Msh4$^{-/-}$ males exhibited normal sexual behavior and aggression, but were infertile. The testis weights of Msh4$^{-/-}$ adult males was only about 50% of wild type and closer analysis revealed no spermatozoa within the epididymides of Msh4$^{-/-}$ adult males nor within the seminiferous tubular lumen of their testes (FIGS. 3B,D). By contrast, Msh4$^{+/+}$ adult male littermates had normal numbers of epididymal spermatozoa and numerous spermatozoa within the seminiferous tubules, as identified by the sperm tails protruding into the tubular lumen (FIGS. 3A, C, arrowheads). To investigate the progression of the first meiotic wave in Msh4$^{+/+}$ and Msh4$^{-/-}$ males, the appearance and progression of germ cells through meiosis was assessed morphologically at day 23 pp, representing the time when the first meiosis I is completed. The seminiferous tubules of Msh4$^{+/+}$ males contained an abundance of meiotic germ cells, ranging from early spermatogonia, flattened against the basement membrane of the tubule, to spermatocytes entering and progressing through prophase I (FIG. 3E). These meiosis I cells were readily identified by their enlarged size, their gradual loss of the signal for GCNA1, a germ cell specific during mitosis and meiosis whose loss is indicative of progression to pachynema (Enders, G. C. et al. (1994) *Dev Biol* 163: 331–340), and their position further towards the lumen of the seminiferous tubules (FIG. 3E). Some differentiating spermatids were also apparent within tubules of mMsh4$^{+/+}$ males, indicating the completion of meiosis II in these cells (FIG. 3E). In contrast, even during the first wave of meiosis between day 13 and 26 pp, seminiferous tubules of Msh4$^{-/-}$ males exhibited a severe depletion of spermatocytes, but not of primary spermatogonia (FIG. 3F). Cells further in towards the lumen of the seminiferous tubules were densely stained with GCNA1 and remained small as compared to those cells seen within the tubules of wild-type males. No luminal cells appeared to be at meiotic stages beyond zygonema. In addition, many cells appeared to be apoptotic as assessed by routine morphological criteria. Thus, by adulthood, seminiferous tubules of Msh4$^{+/+}$ males contained a cellular profile representative of all stages of the spermatogenic wave (FIG. 3A), while the tubules of Msh4$^{-/-}$ males were devoid of many spermatogenic cells, having lost most of the resident type A and B spermatogonia and all of the spermocytes (FIG. 3B). Many seminiferous tubules of adult Msh4$^{-/-}$ males contained only a single layer of spermatogonia and Sertoli cells (FIG. 3B). Interestingly, the interstitial areas of the testes of Msh4$^{-/-}$ males appeared to contain many more Leydig cells (LC, FIGS. 3B, D) than those of wild-type males (FIGS. 3A,C).

Example 4

Chromosome Pairing Analysis in Male Germ Cells

Figure 4A:
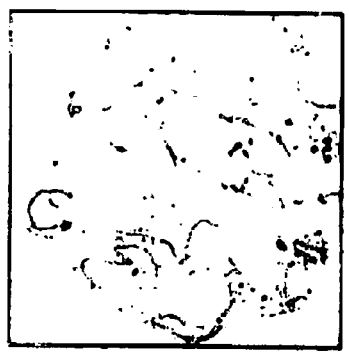
FIG. 4 depicts the results from the analysis of chromosome spreads from spermatocytes of Msh4$^{+/+}$ and Msh4$^{-/-}$ males. Panels A–D represent electron micrographs of silver stained chromosome spreads from spermatocytes of wild type (A) and Msh4$^{-/-}$ homozygous mutant (C-D) males, showing small degree of pairing in the Msh4$^{-/-}$ males compared to complete synapsis of chromsomes from spermatocytes of Msh4$^{+/+}$ males. Arrows indicate non-homologous pairing between two (C) or more (D) chromosomes, arrowheads indicate regions of apparent homologous pairing (in panels C and D). Panels E and F represent silver stained chromosome spreads from spermatocytes taken from Msh5$^{-/-}$ (E) and Msh4$^{-/-}$/Msh5$^{-/-}$ (F) males are shown for comparison, showing less pairing than in chromosome spreads from Msh4$^{-/-}$ spermatocytes. Panels G and H depict immunofluorescent co-localization of RAD51 (green) and the axial element/synaptonemal complex protein, COR1 (white) on chromosome spreads from day 23 pp spermatocytes. P, pachynema; Z, zygonema Yellow arrows indicate regions of pairing, and coincident loss of RAD51 foci at zygonema in Msh4$^{+/+}$ spermatocytes (G), while RAD51 localization on chromosomes of Msh4$^{-/-}$ spermatocytes remains high (H).
Figure 4B:
Figure 4C:
Figure 4D:
Figure 4E:
Figure 4F:

Analysis of meiotic chromosomes in Msh4$^{-/-}$ males revealed severe abnormalities in pairing at the zygotene stage of prophase I, with most chromosomes failing to undergo any degree of pairing and/or synapsis. However, most of the nuclei showed at least some signs of chromosomal interactions. At day 23 pp, when most (>90%) spermatocyte nuclei from wild-type males contain bivalent chromosomes in late zygonema or pachynema (FIG. 4A, Table 1), less than 70% of spermatocyte nuclei from Msh4$^{-/-}$ males contain any paired chromosomes (FIGS. 4B, C, D; Table 1). Of the Msh4$^{-/-}$ cells that did show chromosome pairing, between 2 to 3 (mean=2.74±0.23) chromosomes per cell showed some degree of pairing. However, most pairing was between non-homologous chromosomes as revealed by interactions between chromosomes of different lengths (FIGS. 4C, D; arrows). The small degree of homologous pairing that does occur is limited and rarely apparent across the entire length of the chromosomes FIGS. 4C, D; arrowheads). Occasionally, homologous pairing was evident at one or both ends of a chromosome (FIG. 4D, arrows), while some chromosomes were paired intermittently along their entire length (FIG. 4D, arrowhead). Chromosomes from Msh4$^{-/-}$ males were never condensed, while pairing in wild-type spermatocytes was always accompanied by chromosome condensation. The degree of chromosomal interactions in Msh4$^{-/-}$ spermatocytes was significantly more advanced than that seen in spermatocytes taken from either Msh5$^{-/-}$ or Msh4$^{-/-}$/Msh5$^{-/-}$ males (FIGS. 4E, F; Edelmann et al. (1999) Nat Genet 21:123–127), but remained significantly disrupted when compared to wild-type littermates (Table 1).

Figure 4G:
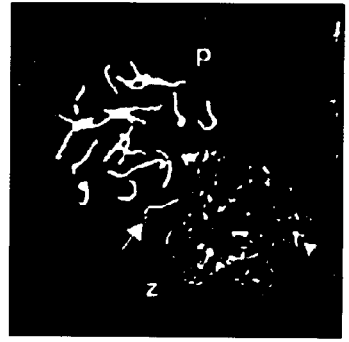
Figure 4H:
Figure 6A:
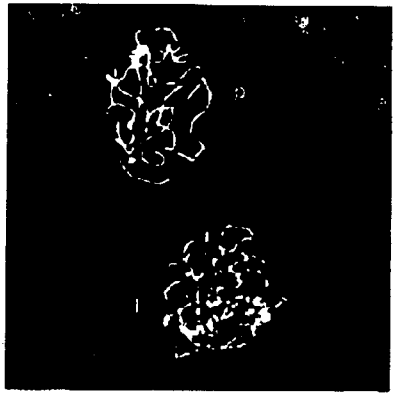
FIG. 6 depicts an immunofluorescent localization of COR1 and RAD51 on meiotic chromosomes from Msh4$^{+/+}$ and Msh4$^{-/-}$ females. The synaptonemal complex protein, COR1, and the RecA homolog, RAD51, were imunolocalized on chromosome spreads from oocytes at e19. COR1 immunofluorescence is shown in white, and RAD51 foci are localized in green. Panels A and B represent chromosome spreads from wildtype oocytes at early zygonema (A, lower nucleus), late zygonema (B) and pachynema (A, top nucleus). Panels C and D represent chromosome spreads from Msh4$^{-/-}$ oocytes at zygonema, showing at least partial synapsis of chromosomes (C, D, arrows) and the coincident loss of RAD51 colocalization.
Figure 6B:
Figure 6C:
Figure 6D:
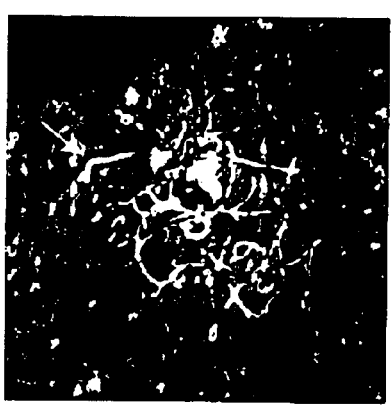

The association of the RecA homolog, RAD51, on unpaired chromosomes at leptonema and zygonema, and loss of such association upon homologous pairing, is now well established (Roccmill et al. (1995) Genes Dev 9:2684–2695; Barlow et al. (1998) Development 125:40074017). To assess the localization of this recombination protein on meiotic chromosomes in the absence of MSH4, co-immunofluorescence was performed using rabbit anti-mouse RAD51 and a mouse monoclonal antibody raised against the synaptonemal complex protein, COR1. As expected, RAD51 foci were readily detectable on chromosomes from wild-type spermatocytes at zygonema (FIG. 4G), but were lost as pairing proceeded (FIG. 4G, arrow) and completely absent by pachynema, a time when synapsis is complete. By contrast, the failure of chromosomal pairing in spermatocytes from Msh4$^{-/-}$ males was associated with increased localization of RAD51 foci on the meiotic chromosomes (FIG. 4H).

TABLE 1

Quantitation of pairing between meiotic chromosomes in Msh4$^{-/-}$, Msh5$^{-/-}$ and Msh4$^{-/-}$/Msh5$^{-/-}$ spermatocytes.

|  | Msh4+/+ | Msh4-/- | Msh5-/- | Msh4-/- Msh5-/- |
|---|---|---|---|---|
| % nuclei with 100% pairing | 64.9[1] (48/74) | 0 | 0 | 0 |
| % nuclei with no pairing | 9.4[2] (7/74) | 31 (18/58) | 90 (54/60) | 92 (46/50) |
| % nuclei with partial pairing | 25.7[3] (19/74) | 69 (40/58) | 10 (6/60) | 8 (4/50) |
| Analysis of partially paired chromosomes: | | | | |
| % non-paired chromosomes | 0 (0/760) | 86.0 (1376/1600) | 89.6 (251/240) | 90.6 (145/160) |
| % homologous partial pairing | 100 (760/760) | 7.1 (114/1600) | 6.25 (15/240) | 0 (0/160) |
| % non homologous pairing | 0 | 6.9 (110/1600) | 4.2 (10/240) | 9.4 (15/160) |
| Statistical analysis of pairing trends between genotypes: | | | | |
| $\chi^2$ comparison with Msh4$^{-/-}$ | P < 0.0001 | — | P < 0.0001 | P < 0.0001 |
| $\chi^2$ comparison with Msh5$^{-/-}$ | P < 0.0001 | P < 0.0001 | — | ns |

(p = 0.09)
Values are %, with n values in parentheses. Total numbers of chromosomes shown in the middle panel of the table are obtained by multiplying 40 (total number of chromosomes per cell) by the number of nuclei showing some pairing. Chi-square analyses were performed between different pairs of groups and the results are presented in the lower panel of the table: ns not significant.
[1]Represents nuclei at pachynema;
[2]Represents nuclei at leptonema;
[3]Represents nuclei at zygonema (with all chromosomes being partially paired).

Example 5

Analysis of Female Meiosis and Ovarian Development in Msh4$^{-/-}$ Females

Meiosis I occurs synchronously in female oogonia from e16 until birth in mice, after which time the oocytes enter a period of dictyate arrest just after pachynema. To analyze the progression of this first stage of meiosis I, ovaries from Msh4$^{+/+}$ and Msh4$^{-/-}$ females were removed during the neonatal period (e18 through to day 4 pp). Staining of germ cells with an antibody against GCNAL revealed a steady loss of germ cells in Msh4$^{-/-}$ females soon after birth (FIGS. 5A–F). At e18, the number of GCNA1-positive cells in Msh4$^{+/+}$ and Msh4$^{-/-}$ ovaries was similar (FIGS. 5A, B). By day 2 pp, the earliest signs of follicular development as part of ovarian reorganization were apparent in Msh4$^{+/+}$ ovaries (FIG. 5C, arrows), while many of the oogonia in Msh4$^{-/-}$ cells had already been lost (FIG. 5D). By day 4 pp, when all of the remaining oocytes in Msh4$^{+/+}$ ovaries were enclosed by readily identifiable primordial follicles (FIG. 5E, arrows), the vast majority of oocytes in Msh4$^{-/-}$ ovaries had been lost (FIG. 5F), indicating a loss of oocytes prior to dictyate arrest in the Msh4$^{-/-}$ females. To assess the consequences of oocyte loss in Msh4$^{-/-}$ females, ovaries were taken at 4, 16 and 28 weeks of life. In contrast to the oocyte-rich ovary in 4 week old Msh4$^{+/+}$ females (FIG. 5G), Msh4$^{-/-}$ females had very small ovaries containing few if any oocytes at this age (FIG. 5H). Often, many divergent morphologies were present within the same female, as is the case for the pair of ovaries shown in FIGS. 7H (i, ii). Immunohistochemical analysis using an antibody directed against P450-side chain cleavage enzyme revealed that these structures were not producing steroids, but were epithelial in origin, as demonstrated by immunohistochemical staining with an anti-cytokeratin antibody. These ovarian structures were completely encased within their ovarian bursas and were attached to apparently normal oviductal and uterine structures. By 7 months of age, the ovaries of Msh4$^{-/-}$ females were virtually non-existent, or consisted of massively convoluted tissue structures, with no resemblance to the wild-type ovaries at the same age. These structures occasionally, but not always, contained a single or a number of large fluid and blood-filled cysts (FIG. 7H).

Example 6

Chromosomal Pairing in Msh4$^{-/-}$ Oocytes

Analysis of chromosomal pairing in oocytes firm Msh4$^{+/+}$ and Msh4$^{-/-}$ females was performed at e19 by immunofluorescence because the extremely small amount of tissue precluded the use of the silver staining technique. However, these analyses demonstrated clearly that the oocytes from both Msh4$^{+/+}$ and Msh4$^{-/-}$ ovaries enter leptonema, and acquire both their initial synaptonemal complex proteins and at least one key recombination nodule protein, RAD51 (FIG. 6). As in the males, the number of RAD51 foci on meiotic chromosomes remained higher in the Msh4$^{-/-}$ oocytes, compared to wild-type oocytes (FIGS. 6A, B), indicative of a failure to undergo complete pairing and to enter pachynema FIGS. 6C, D). In those regions of chromosomes that did undergo pairing, RAD51 foci were lost (FIGS. 6C, D arrows), indicating that the pairing failure itself might be responsible for the persistence of RADS 51 foci. Pairing of homologous chromosomes appeared to be a more frequent occurrence in Msh4 mutant oocytes than in Msh4 mutant spermatocytes, although the small amount of tissue available in the embryonic ovaries precluded the possibility of a more quantitative assessment of pairing in the female germ cells.

Example 7

MSH4 and MSH5 Function in the Same Genetic Pathway

The comparison of the meiotic phenotype between Msh4$^{-/-}$ and Msh5$^{-/-}$ mice revealed that both MutS homologs are required in the early stages of meiosis I and are essential for normal chromosome synapsis during zygonema. To investigate if mammalian MSH4 and MSH5 function in the same epistasis group, double mutant Msh4$^{-/-}$/Msh5$^{-/-}$ mice were generated. As with the single mutant mice, no adverse phenotype was observed with regard to the viability and survival of Msh4$^{-/-}$/Msh5$^{-/-}$ mice and no notable somatic phenotype was apparent. Both male and female double homozygous mutant mice were infertile. The degree of chromosomal pairing during meiosis I in spermatocytes was similar to that seen in Mshk5$^{-/-}$ mice, in that less than 10% of nuclei contained chromosomes with any degree of pairing, and no chromosomal condensation was apparent (FIGS. 4E, F; Table 1). The similarity in meiotic phenotype between Msh5$^{-/-}$ and Msh4$^{-/-}$/Msh5$^{-/-}$ mice indicates that mammalian MSH5 functions upstream of MSH4 within the same epistasis group and both are required at the same time in meiosis to ensure proper chromosome synapsis.

Example 8

MSH4 and MSH5 Interact in a Mammalian Two-hybrid Assay

For the mammalian two-hybrid assay, Cos7 cells were plated in 96-well plates at 3×10$^6$ cells per well in MEM (minimal essential medium) or other compatible growth medium. (Other concentrations of cells were also tested and found to be effective). Transfections were performed with Lipofectamine 2000 (Gibco-BRL) transfection reagent using the conditions recommended by the supplier. The two hybrid plasmids containing MSH4 or MSH5 were used in conjunction with a luciferase reporter plasmid at a 1:1:1 ratio. A CMV-β-Gal plasmid was used for normalization of luciferase units between different wells. Cells were harvested at 16–48 hours following transfection. The cells in each well were lysed by the addition of 50 μl of lysis buffer and assayed using standard methods.

Figure 7:
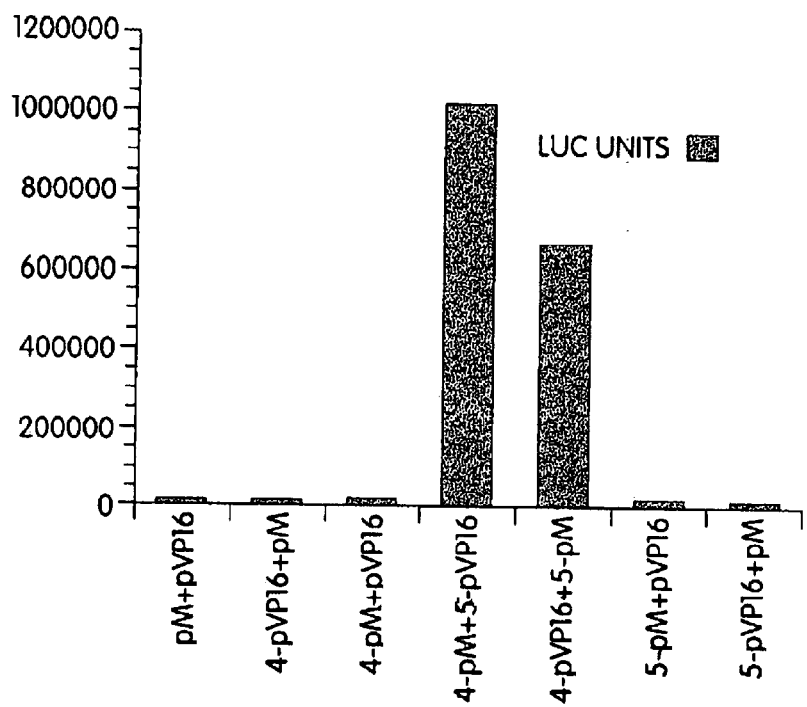
FIG. 7 is a graph depicting the results from a mammalian two-hybrid interaction analysis using the pM and pVp16 vector system in a COS7 cel line.

The results, presented in FIG. 7, demonstrate that there is an interaction between MSH4 and MSH5, as measured by luciferase (LUC) units.

Example 9

MSH4 and MSH5 Interact in a Yeast Two-hybrid Assay

Figure 8:
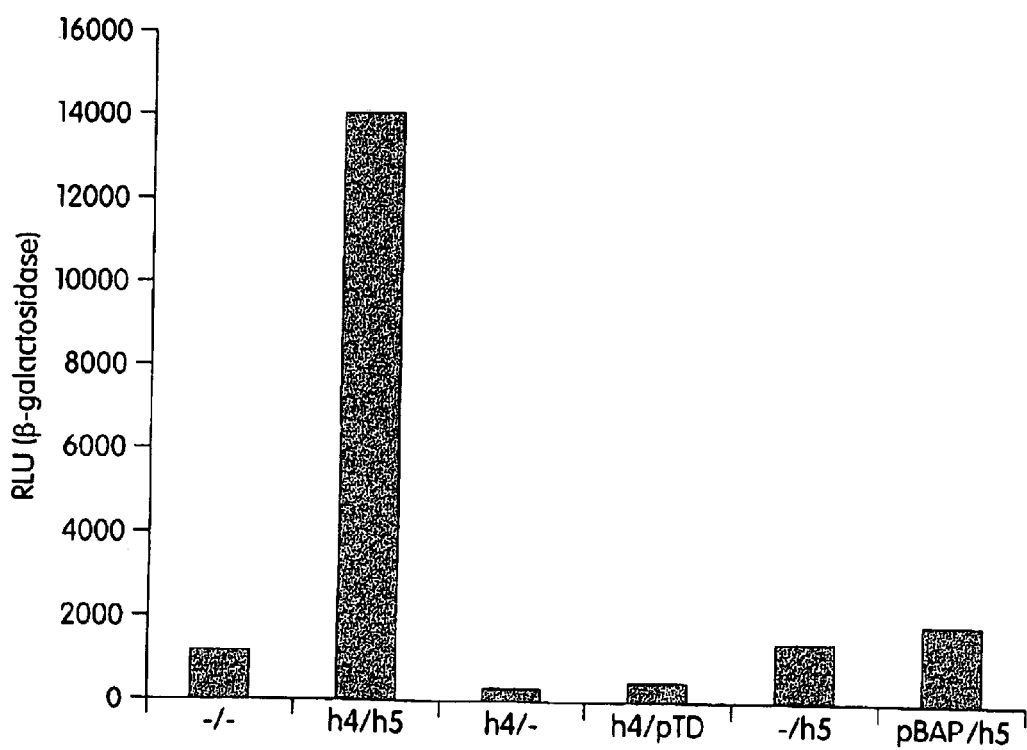
FIG. 8 is a graph depicting the results from a yeast two-hybrid assay indicating that there is an interaction between human MSH4 and human MSH5.

A yeast two-hybrid (Y2H) assay was developed for the purpose of targeting the interaction between human MSH4 (h4) and human MSH5 (h5). In the Y2H, h4 is in the GAL4 DNA-binding domain vector (DBD) and h5 is in the GAL4 activation domain vector (AD). An integrated copy of the GAL4$_{UAS}$-β-galactosidase reporter was used to monitor the interaction. Interaction strength was measured by β-galactosidase activity, which is reported as relative light units (RLU). As part of the validation of the interaction between h4 and h5 the respective proteins were analyzed alone and in combination with unrelated proteins. In these validation experiments, interaction strength, as measured RLUs was normalized to cell density. As shown in FIG. 8, the interaction strength of h4/h5, relative to the controls, indicates specificity of the interaction and suitability for screening inhibitors of the interaction. (−/−, empty vectors (DBD/AD); pTD, large T-antigen; pBAP, β-amyloid protein).

Example 10

Presence of MSH4 Containing Complexes in Mouse Spermatocytes

Immunoprecipitation of mouse testicular lysates with anti–MSH4 antibody and Western blotting with anti–MSH5 antibody have shown interactions between MSH4 and MSH5. These were confirmed by a reciprocal immunoprecipitation experiment. Using immunoprecipitation with anti-MLH1 and Western blotting with MSH4 an interaction between these proteins was shown, that was absent in the MSH4 null cells. In contrast, immunoprecipitation with anti–RAD51 antibody showed interaction with MSH4 and MSH5 but not with MLH1. These data provide compelling evidence for two complexes in mammalian spermatocytes. The first consisting of at least, MSH4:MSH5:RAD51, while the second has MSH4:MSH5:MLH1. Since MLH1 is not expressed in leptonema and RAD51 is largely lost by mid pachytene (see Cohen, P. E. and Pollard, J. W. (2001) Bioessays 23:996–1009) this demonstrates that complex one is present uniquely in leptonema while complex 2 is present at mid-pachytene until at least, meiosis (M1). In addition, we have evidence that MSH4 and MSH5 are present at M2 suggesting that these proteins may have additional functions later in meiosis and that these proteins could also act as contraceptive targets at this stage of meiosis.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound that modulates the interaction between MSH4 and MSH5, comprising contacting MSH4 with a test compound and determining the ability of said test compound to modulate the interaction between MSH4 and MSH5, thereby identifyng a compound that modulates the interaction between MSH4 and MSH5.

2. The method of claim 1, wherein said compound inhibits the interaction between MSH4 and MSH5.

3. A method for identifying a candidate contraceptive compound, comprising contacting MSH4 with a test compound and determining the ability of said test compound to inhibit the interaction between MSH4 and MSH5, thereby identifying a candidate contraceptive compound.

4. The method of one of claim 1 or 3, wherein MSH4 is contacted directly with a test compound.

5. A method for identifying a compound that modulates the interaction between MSH4 and MSH5, comprising contacting a cell expressing MSH4 and MSH5 with a test compound and determining the ability of said test compound to modulate the interaction between MSH4 and MSH5, thereby identifying a compound that modulates the interaction between MSH4 and MSH5.

6. A method for identifying a candidate contraceptive compound, comprising contacting a cell expressing MSH4 and MSH5 with a test compound and determining the ability of said test compound to inhibit the interaction between MSH4 and MSH5, thereby identifying a candidate contraceptive compound.

7. The method of one of claims 1, 3, 5, or 6, wherein said test compound is a small molecule.

8. The method of one of claims 1, 3, 5, or 6, wherein said test compound is a peptide.

9. The method of one of claims 1, 3, 5, or 6, wherein said test compound is a nucleic acid molecule.

10. The method of one of claims 1, 3, 5, or 6, wherein said compound is an anti–MSH4 antibody.

11. The method of one of claims 5 or 6, wherein said cell is an oocyte or a spermatocyte.

\* \* \* \* \*